(12) United States Patent
Dorsch et al.

(10) Patent No.: US 9,102,675 B2
(45) Date of Patent: Aug. 11, 2015

(54) 3-CYANOARYL-1H-PYRROLO[2,3-B] PYRIDINE DERIVATIVES

(71) Applicant: MERCK PATENT GMBH, Darmstadt (DE)

(72) Inventors: Dieter Dorsch, Ober-Ramstadt (DE); Guenter Hoelzemann, Seeheim-Jugenheim (DE); Hans-Michael Eggenweiler, Darmstadt (DE); Paul Czodrowski, Friedberg (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/359,705

(22) PCT Filed: Oct. 30, 2012

(86) PCT No.: PCT/EP2012/004543
§ 371 (c)(1),
(2) Date: May 21, 2014

(87) PCT Pub. No.: WO2013/075785
PCT Pub. Date: May 30, 2013

(65) Prior Publication Data
US 2014/0323481 A1    Oct. 30, 2014

(30) Foreign Application Priority Data
Nov. 22, 2011    (DE) .......................... 10 2011 119 127

(51) Int. Cl.
| | | |
|---|---|---|
| *C07D 471/04* | (2006.01) | |
| *A61K 31/437* | (2006.01) | |
| *A61K 31/496* | (2006.01) | |
| *A61K 31/5377* | (2006.01) | |
| *A61K 45/06* | (2006.01) | |

(52) U.S. Cl.
CPC ............ *C07D 471/04* (2013.01); *A61K 31/437* (2013.01); *A61K 31/496* (2013.01); *A61K 31/5377* (2013.01); *A61K 45/06* (2013.01)

(58) Field of Classification Search
CPC ............................ C07D 471/04; A61K 31/437
See application file for complete search history.

(56) References Cited

U.S. PATENT DOCUMENTS

| | | |
|---|---|---|
| 7,361,763 B2 | 4/2008 | Arnold et al. |
| 7,507,826 B2 | 3/2009 | Salituro et al. |
| 7,582,637 B2 | 9/2009 | Arnold et al. |
| 7,906,648 B2 | 3/2011 | Arnold et al. |
| 8,188,281 B2 | 5/2012 | Salituro et al. |
| 8,242,280 B2 | 8/2012 | Chen et al. |
| 8,501,446 B2 | 8/2013 | Salituro et al. |
| 8,722,889 B2 | 5/2014 | Salituro et al. |
| 2006/0030583 A1 | 2/2006 | Arnold et al. |
| 2007/0043063 A1 | 2/2007 | Salituro et al. |
| 2008/0221119 A1 | 9/2008 | Arnold et al. |
| 2008/0261921 A1 | 10/2008 | Chen et al. |
| 2009/0176763 A1 | 7/2009 | Salituro et al. |
| 2009/0306056 A1 | 12/2009 | Arnold et al. |
| 2012/0258958 A1 | 10/2012 | Salituro et al. |
| 2013/0345197 A1 | 12/2013 | Salituro et al. |

FOREIGN PATENT DOCUMENTS

| | | |
|---|---|---|
| WO | 2005095400 A1 | 10/2005 |
| WO | 2006015123 A1 | 2/2006 |
| WO | 2008124848 A1 | 10/2008 |

OTHER PUBLICATIONS

International Search Report for PCT/EP2012/004543 dated Jan. 28, 2013.

*Primary Examiner* — David K O Dell
(74) *Attorney, Agent, or Firm* — Millen, White, Zelano, Branigan, P.C.

(57) ABSTRACT

Compounds of the formula (I) in which $R^1$, $R^2$, X and Y have the meanings indicated in claim 1, are inhibitors of TBK1 and IKKε and can be employed, inter alia, for the treatment of cancer and inflammatory diseases.

14 Claims, No Drawings

3-CYANOARYL-1H-PYRROLO[2,3-B] PYRIDINE DERIVATIVES

BACKGROUND OF THE INVENTION

The object of the invention was to find novel compounds having valuable properties, in particular those which can be used for the preparation of medicaments.

The present invention relates to pyridine compounds which are capable of inhibiting one or more kinases. The compounds are used in the treatment of a multiplicity of disorders, including cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The present invention relates to compounds and to the use of compounds in which the inhibition, regulation and/or modulation of signal transduction by receptor kinases plays a role, furthermore to pharmaceutical compositions which comprise these compounds and to the use of the compounds for the treatment of kinase-induced diseases. Since protein kinases regulate virtually every cellular process, including metabolism, cell proliferation, cell differentiation and cell survival, they are attractive targets for therapeutic intervention in the case of various conditions. For example, cell-cycle control and angiogenesis, in which protein kinases play a key role, are cell processes associated with numerous conditions, such as, but not limited to, cancer, inflammatory diseases, abnormal angiogenesis and diseases related thereto, atherosclerosis, macular degeneration, diabetes, obesity and pain.

In particular, the present invention relates to compounds and to the use of compounds in which the inhibition, regulation and/or modulation of signal transduction by TBK1 and IKKε plays a role.

One of the principal mechanisms by which cell regulation is effected is through the transduction of extracellular signals across the membrane, which in turn modulate biochemical pathways in the cell. Protein phosphorylation represents one process by which intracellular signals are propagated from molecule to molecule, finally resulting in a cell response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a widespread process in cells and since cell phenotypes are mostly influenced by the activity of these pathways, it is currently thought that a number of conditions and/or diseases are attributable to either aberrant activation or functional mutations in the molecular components of kinase cascades. Consequently, considerable attention has been paid to the characterisation of these proteins and compounds which are able to modulate their activity (review articles see: Weinstein-Oppenheimer et al. Pharma. &. Therap., 2000, 88, 229-279).

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4, and the RNA helicases RIG-I and MDA-5 and result in activation of the TRIF-TBK1/IKKE-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene. In addition, the authors were able to show that IKKε is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a 251,000 cDNA gene library, Korherr et al. identified precisely three genes, TRIF, TBK1 and IRF3, that are typically involved in the innate immune defence as proangiogenic factors [C. Korherr et al., PNAS, 103, 4240-4245, 2006]. In 2006, Chien et al. [Y. Chien et al., Cell 127, 157-170, 2006] published that TBK1−/− cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase or the generation of an activity level which can be correlated with a cell proliferation disease (i.e. the severity of one or more symptoms of the cell proliferation disease increases with increasing kinase level) the bioavailability of a protein kinase may also be influenced by the presence or absence of a set of binding proteins of this kinase.

IKKε and TBK1 are highly homologous Ser/Thr kinases which play a crucial role in the innate immune response through induction of type 1 interferons and other cytokines. These kinases are stimulated in response to viral/bacterial infection. Immune response to viral and bacterial infections involves the binding of antigens, such as bacterial lipopolysaccharide (LPS), viral double-stranded RNA (dsRNA), to Toll-like receptors, subsequent activation of the TBK1 pathway. Activated TBK1 and IKKε phosphorylate IRF3 and IRF7, which triggers the dimerisation and nuclear translocation of these interferonregulating transcription factors, ultimately inducing a signalling cascade leading to IFN production.

Recently, IKKε and TBK1 have also been implicated in cancer. It has been shown that IKKε cooperates with activated MEK to transform human cells. In addition, IKKε is frequently amplified/overexpressed in breast cancer cell lines and tumours originating from patients. TBK1 is induced under hypoxic conditions and expressed at significant levels in many solid tumours. Furthermore, TBK1 is necessary to support oncogenic Ras transformation, and TBK1 kinase activity is increased in transformed cells and is necessary for their survival in culture. It has likewise been found that TBK1 and NF-kB signalling are essential in KRAS-mutated tumours. TBK1 has been identified as a synthetic lethal partner of oncogenic KRAS.

Lit.:

Y.-H. Ou et al., Molecular Cell 41, 458-470, 2011;

D. A. Barbie et al., Nature, 1-5, 2009.

WO 2011/046970 A1 describes the use of TBK1 and/or IKKε inhibitors for the treatment of various diseases, such as rheumatoid arthritis (RA), systemic lupus erythematosus (SLE), Sjorgren's syndrome, Aicardi-Goutiéres syndrome chilblain lupus, retinal vasculopathy and cerebral leukodystrophy (RVCL), systemic sclerosis, myositis, psoriasis, chronic obstructive pulmonary disease (CPD), inflammatory bowel disease (IBD), obesity, insulin resistance, type 2 diabetes (NIDDM), metabolic syndrome, cancer diseases, Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of chronic diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined. The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

In addition, the compounds according to the invention can be used to achieve additive or synergistic effects in certain existing cancer chemotherapies and radiotherapies and/or to restore the efficacy of certain existing cancer chemotherapies and radiotherapies.

The term "method" refers to manners, means, techniques and procedures for accomplishing a given task, including, but not limited to, those manners, means, techniques and procedures which are either known to the person skilled in the art in the chemical, pharmacological, biological, biochemical and medical area or can easily be developed by him from known manners, means, techniques and procedures b.

The term "administration" as used here refers to a method for bringing a compound of the present invention and a target kinase together in such a way that the compound is able to affect the enzyme activity of the kinase either directly, i.e. by interaction with the kinase itself, or indirectly, i.e. by interaction with another molecule on which the catalytic activity of the kinase is dependent. As used here, administration can be carried out either in vitro, i.e. in a test tube, or in vivo, i.e. in cells or tissues of a living organism.

The term "treatment" here encompasses abrogation, substantial inhibition, slowing or reversal of the progress of a disease or disorder, substantial amelioration of the clinical symptoms of a disease or disorder or substantial prevention of the occurrence of clinical symptoms of a disease or disorder.

The term "prevention" here refers to a method for blocking an organism from acquiring a disorder or disease in the first place.

For any desired compound used in this invention, a therapeutically effective amount, also referred to here as a therapeutically effective dose, can be calculated initially from cell culture assays. For example, a dose can be formulated in animal models to achieve a circulating concentration range that includes the IC50 or the IC100 as determined in cell cultures. This information can be used to determine useful doses for humans more accurately. Initial dosages can also be calculated from in-vivo data. Using these initial guidelines, an average person skilled in the art could determine an effective dosage for humans.

Moreover, the toxicity and therapeutic efficacy of the compounds described here can be determined by standard pharmaceutical procedures on cell cultures or experimental animals, for example by determining the LD50 and the ED50. The dose ratio between toxic and therapeutic effect is the therapeutic index and can be expressed as the ratio between LD50 and ED50. Compounds which exhibit a high therapeutic index are preferred. The data obtained from these cell culture assays and animal studies can be used to formulate a dosage range which is not toxic for human use. The dosage of such compounds is preferably in bloodstream concentration ranges which include the ED50 with little or no toxicity. The dosage may vary within this range depending on the dosage form employed and the route of administration used. The precise formulation, route of administration and dosage can be selected by the individual physician taking into account the patient's condition (see, for example, Fingl et al., 1975, in: The Pharmacological Basis of Therapeutics, Chapter 1, page 1).

Dosage amount and interval may be adjusted individually to provide plasma levels of the active compound which are sufficient to obtain a therapeutic effect. Usual patient dosages for oral administration are in the range from about 50-2000 mg/kg/day, generally from about 100-1000 mg/kg/day, preferably from about 150-700 mg/kg/day and particularly preferably from about 250-500 mg/kg/day.

Therapeutically effective serum levels are preferably achieved by administration of multiple doses per day. In the case of local administration or selective uptake, the effective local concentration of the medicament may not be related to the plasma concentration. The person skilled in the art will be able to optimise therapeutically effective local dosages without undue experimentation.

Preferred diseases or disorders for the prevention, treatment and/or investigation of which the compounds described here may be useful are cell proliferative disorders, in particular cancer, such as, but not limited to, papilloma, blastoglioma, Kaposi's sarcoma, melanoma, lung cancer, ovarian cancer, prostate cancer, squamous cell carcinoma, astrocytoma, head cancer, neck cancer, skin cancer, liver cancer, bladder cancer, breast cancer, lung cancer, uterine cancer, prostate cancer, testicular carcinoma, colorectal cancer, thyroid cancer, pancreatic cancer, stomach cancer, hepatocellular carcinoma, leukaemia, lymphoma, Hodgkin's disease and Burkitt's disease.

PRIOR ART

Other benzonitrile derivatives are described as TBK1 and/or IKKε inhibitors in WO 2011/046970 A1.

WO 2005/095400 describes other azaindole kinase inhibitors.

WO2006/015123 describes other pyrrolopyridine kinase modulators.

Further heterocyclic derivatives and their use as antitumour agents have been described in WO 2007/129044.

Further pyridine and pyrazine derivatives have been described in the use for the treatment of cancer in WO 2009/053737 and for the treatment of other diseases in WO 2004/055005.

Further heterocyclic derivatives have been disclosed as IKKε inhibitors in WO 2009/122180.

Pyrrolopyrimidines have been described as IKKε and TBK1 inhibitors in WO 2010/100431.

Pyrimidine derivatives have been described as IKKε and TBK1 inhibitors in WO 2009/030890.

SUMMARY OF THE INVENTION

The invention relates to compounds of the formula I

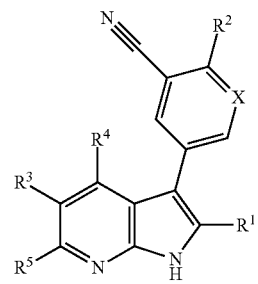

in which
X denotes CH or N,
$R^1$ denotes H, A or Cyc,
$R^2$ denotes O[C($R^6$)$_2$]$_n$Het$^1$, NR$^6$[C($R^6$)$_2$]$_n$Het$^1$, O[C($R^6$)$_2$]$_n$Cyc or NR$^6$[C($R^6$)$_2$]$_n$Cyc,
$R^3$ denotes H, Hal, A, OR$^6$, N(R$^6$)$_2$, O[C(R$^6$)$_2$]$_m$N(R$^6$)$_2$, O[C(R$^6$)$_2$]$_n$Het$^2$, NR$^6$[C(R$^6$)$_2$]$_m$N(R$^6$)$_2$, NR$^6$[C(R$^6$)$_2$]$_n$Het$^2$, Ar or Het$^2$,
$R^4$ denotes H or OR$^6$,
$R^5$ denotes H or OR$^6$,
$R^6$ denotes H or unbranched or branched alkyl having 1-6 C atoms, in which 1-7H atoms may be replaced by F,
Het$^1$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by Hal, CN, OH, OA, COOA, CONH$_2$, S(O)$_n$A, S(O)$_n$Ar, COA, A or =O,
Het$^2$ denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by by Hal, A, [C(R$^6$)$_2$]$_p$OR$^6$, [C(R$^6$)$_2$]$_p$N(R$^6$)$_2$, [C(R$^6$)$_2$]$_p$Het$^1$, NO$_2$, CN, [C(R$^6$)$_2$]$_p$COOR$^6$, CON(R$^6$)$_2$, NR$^6$COA, NR$^6$SO$_2$A, SO$_2$N(R$^6$)$_2$, S(O)$_n$A, COHet$^j$, O[C(R$^6$)$_2$]$_p$N(R$^6$)$_2$, O[C(R$^6$)$_2$]$_p$Het$^1$, NHCOOA, NHCON(R$^6$)$_2$, NHCOO[C(R$^6$)$_2$]$_p$N(R$^6$)$_2$, NHCOO[C(R$^6$)$_2$]$_p$Het$^1$, NHCONH[C(R$^6$)$_2$]$_p$N(R$^6$)$_2$, NHCONH[C(R$^6$)$_2$]$_p$Het$^1$, OCONH[C(R$^6$)$_2$]$_p$N(R$^6$)$_2$, OCONH[C(R$^6$)$_2$]$_p$Het$^1$, CHO, COA, =S, =NR$^6$ and/or =O, Ar denotes phenyl or naphthyl, each of which is unsubstituted or mono-, di- or trisubstituted by Hal, A, [C(R$^6$)$_2$]$_p$OR$^6$, [C(R$^6$)$_2$]$_p$N(R$^6$)$_2$, [C(R$^6$)$_2$]$_p$Het$^1$, NO$_2$, CN, [C(R$^6$)$_2$]$_p$COOR$^6$, CON(R$^6$)$_2$, NR$^6$COA, NR$^6$SO$_2$A, SO$_2$N(R$^6$)$_2$, S(O)$_n$A, COHet$^1$, O[C(R$^6$)$_2$]$_p$N(R$^6$)$_2$, O[C(R$^6$)$_2$]$_p$Het$^1$, NHCOOA, NHCON(R$^6$)$_2$, NHCOO[C(R$^6$)$_2$]$_p$N(R$^6$)$_2$, NHCOO[C(R$^6$)$_2$]$_p$Het$^1$, NHCONH[C(R$^6$)$_2$]$_p$N(R$^6$)$_2$, NHCONH[C(R$^6$)$_2$]$_p$Het$^1$, OCONH[C(R$^6$)$_2$]$_p$N(R$^6$)$_2$, OCO—H[C(R$^6$)$_2$]$_p$Het$^1$, CHO and/or COA, A denotes unbranched or branched alkyl having 1-10 C atoms, in which one or two non-adjacent CH and/or CH$_2$ groups may be replaced by N, O and/or S atoms and/or, in addition, 1-7H atoms may be replaced by F and/or Cl, Cyc denotes cyclic alkyl having 3, 4, 5, 6 or 7 C atoms which is unsubstituted or monosubstituted by CN or A, Hal denotes F, Cl, Br or I, m denotes 1, 2 or 3, n denotes 0, 1 or 2, p denotes 0, 1, 2, 3 or 4, and pharmaceutically usable salts, tautomers and stereoisomers thereof, including mixtures thereof in all ratios.

The invention also relates to the optically active forms (stereoisomers), salts, the enantiomers, the racemates, the diastereomers and the hydrates and solvates of these compounds. Solvate of the compounds are taken to mean adductions of inert solvent molecules onto the compounds which form owing to their mutual attractive force. Solvate are, for example, mono- or dihydrates or alcoholates.

The invention naturally also relates to the solvates of the salts.

Pharmaceutically usable derivatives are taken to mean, for example, the salts of the compounds according to the invention and also so-called prodrug compounds. Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that a) a compound of the formula II

II in which R$^1$, R$^3$, R$^4$, R$^5$ has the meanings indicated in claim 1,

Y denotes Br or I and

Q denotes a protecting group, is reacted with a compound of the formula III

III in which X and R$^2$ have the meaning indicated in claim 1 and

L denotes a boronic acid radical or a boronic acid ester group, and Q is subsequently cleaved off, or b) in that they are liberated from one of their functional derivatives by treatment with a solvolysing or hydrogenolysing agent, and/or a base or acid of the formula I is converted into one of its salts.

Above and below, the radicals R$^1$, R$^2$, R$^3$, R$^4$, R$^5$ and X have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two CH and/or CH$_2$ groups in A may also be replaced by N, O or S atoms. Thus, A also denotes, for example, 2-methoxyethyl.

A particularly preferably denotes unbranched or branched alkyl having 1-8 C atoms, in which, in addition, one or two non-adjacent CH and/or CH$_2$ groups may be replaced by N and/or O atoms and/or 1-7H atoms may be replaced by F.

Cycloalkyl (cyclic alkyl) denotes cyclopropyl, cyclobutyl, cyclopentyl, cyclohexyl or cycloheptyl.

R$^1$ preferably denotes H or A.

R$^2$ preferably denotes O[C(R$^6$)$_2$]$_n$Het$^1$ or O[C(R$^6$)$_2$]$_n$Cyc.

R$^3$ preferably denotes H, Hal, O[C(R$^6$)$_2$]$_n$Het$^2$, Ar or Het$^2$.

R⁴ particularly preferably denotes H.
R⁵ particularly preferably denotes H.
R⁶ preferably denotes H or methyl.
Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methylaminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar particularly preferably denotes phenyl or naphthyl, each of which is unsubstituted or monosubstituted by $[C(R^6)_2]_p$Het¹ or CN.

Het¹ preferably denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n$A, $S(O)_n$Ar or A.

Het¹ particularly preferably denotes pyrrolidinyl, oxetanyl, piperidinyl, morpholinyl, tetrahydropyranyl or piperazinyl, each of which is unsubstituted or monosubstituted by $S(O)_n$A, $S(O)_n$Ar or A.

Het² preferably denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or monosubstituted by by A, $[C(R^6)_2]_p$OR⁶ or $[C(R^6)_2]_p$Het¹.

Het² particularly preferably denotes piperidinyl, morpholinyl, piperazinyl, pyrazolyl or triazolyl, each of which is unsubstituted or monosubstituted by by A, $[C(R^6)_2]_p$OR⁶ or $[C(R^6)_2]_p$Het¹.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia R² denotes $O[C(R^6)_2]_n$Het¹ or $O[C(R^6)_2]_n$Cyc;
in Ib R³ denotes H, Hal, $O[C(R^6)_2]_n$Het², Ar or Het²;
in Ic Het¹ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n$r, $S(O)_n$Ar or A;
in Id Het² denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or monosubstituted by by A, $[C(R^6)_2]_p$OR⁶ or $[C(R^6)_2]_p$Het¹;
in Ie Ar denotes phenyl or naphthyl, each of which is unsubstituted or monosubstituted by $[C(R^6)_2]_p$Het¹ or CN;
in If A denotes unbranched or branched alkyl having 1-8 C atoms, in which one or two non-adjacent CH and/or CH₂ groups may be replaced by N and/or O atoms and/or, in addition, 1-7H atoms may be replaced by F;
in Ig X denotes CH or N,
R¹ denotes H, A or Cyc,
R² denotes $O[C(R^6)_2]_n$Het¹ or $O[C(R^6)_2]_n$Cyc,
R³ denotes H, Hal, $O[C(R^6)_2]_n$Het², Ar or Het²,
R⁴ denotes H or OR⁶,
R⁵ denotes H or OR⁶,
R⁶ denotes H or methyl,
Het¹ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n$A, $S(O)_n$Ar or A,
Het² denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or monosubstituted by by A, $[C(R^6)_2]_p$OR⁶ or $[C(R^6)_2]_p$Het¹,
Ar denotes phenyl or naphthyl, each of which is unsubstituted or monosubstituted by $[C(R^6)_2]_p$Het¹ or CN,
A denotes unbranched or branched alkyl having 1-8 C atoms, in which one or two non-adjacent CH and/or CH₂ groups may be replaced by N and/or O atoms and/or, in addition, 1-7H atoms may be replaced by F,
Cyc denotes cyclic alkyl having 3, 4, 5, 6 or 7 C atoms which is unsubstituted or monosubstituted by CN or A,
Hal denotes F, Cl, Br or I,
m denotes 1, 2 or 3,
n denotes 0, 1 or 2,
p denotes 0, 1, 2, 3 or 4, and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II with a compound of the formula III.

The compounds of the formula II and of the formula III are generally known. If they are novel, however, they can be prepared by methods known per se.

In the compounds of the formula II, Y preferably denotes I. Q preferably denotes BOC or phenylsulfonyl.

In the compounds of the formula III, L preferably denotes

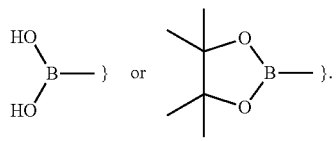

The reaction is carried out under conditions which are known to the person skilled in the art as Suzuki conditions or Suzuki reaction.

Depending on the conditions used, the reaction time is between a few minutes and 14 days, the reaction temperature is between about −10° and 160°, normally between 20° and 150°, particularly preferably between 40° and 100° C. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tertbutanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to DMF and water.

The cleavage of an ether is carried out under methods known to the person skilled in the art.

A standard method of ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be hydrolysed, for example, using acetic acid or using NaOH or KOH in water, water/THF or water/dioxane at temperatures between 0 and 100°.

Alkylations on the nitrogen are carried out under standard conditions, as are known to the person skilled in the art.

The compounds of the formulae I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' denotes an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" denotes a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl, tolyl; aryloxyalkanoyl, such as POA; alkoxycarbonyl, such as methoxycarbonyl, ethoxycarbonyl, 2,2,2-trichloroethoxycarbonyl, BOC, 2-iodoethoxycarbonyl; aralkoxycarbonyl, such as CBZ ("carbobenzoxy"), 4-methoxybenzyloxycarbonyl, FMOC; arylsulfonyl, such as phenylsulfonyl, Mtr, Pbf, Pmc. Preferred amino-protecting groups are BOC and Mtr, furthermore CBZ, Fmoc, benzyl and acetyl.

The NH group of the pyrrolo[2,3-b]pyridine ring system is preferably protected by an indole protecting group during the reactions. Preference is given to BOC or phenylsulfonyl. This protecting group is cleaved off at the end of the reactions.

The phenylsulfonyl group is preferably cleaved off using trifluoroethanol or methanol in THF with addition of an organic or inorganic base.

Suitable bases are organic bases, such as DIPEA, triethylamine, dimethylamine, pyridine or quinoline. Preference is also given to the addition of an alkali-metal or alkaline-earth metal hydroxide, carbonate or bicarbonate or another salt of a weak acid of the alkali or alkaline-earth metals, preferably of potassium, sodium, calcium or caesium.

The expression "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5 N HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

The invention furthermore relates to the compounds of the formula II

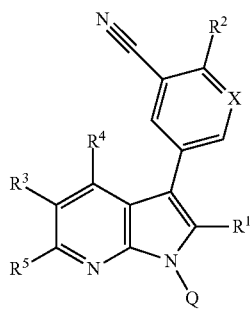

in which
X denotes CH or N,
Q denotes tert-butoxycarbonyl or phenylsulfonyl,
R' denotes H, A or Cyc,
$R^2$ denotes $O[C(R^6)_2]_n$Het$^1$ or $O[C(R^6)_2]_n$Cyc,
$R^3$ denotes H, Hal, $O[C(R^6)_2]_n$Het$^2$, Ar or Het$^2$,
$R^4$ denotes H or $OR^6$,
$R^5$ denotes H or $OR^6$,
$R^6$ denotes H or methyl,
Het$^1$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n$A, $S(O)_n$Ar or A,
Het$^2$ denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or monosubstituted by by A, $[C(R^6)_2]_p$OR$^6$ or $[C(R^6)_2]_p$Het$^1$,
Ar denotes phenyl or naphthyl, each of which is unsubstituted or monosubstituted by $[C(R^6)_2]_p$Het$^1$ or CN,
A denotes unbranched or branched alkyl having 1-8 C atoms, in which one or two non-adjacent CH and/or CH$_2$ groups may be replaced by N and/or O atoms and/or, in addition, 1-7H atoms may be replaced by F,
Cyc denotes cyclic alkyl having 3, 4, 5, 6 or 7 C atoms which is unsubstituted or monosubstituted by CN or A,
Hal denotes F, Cl, Br or I,
m denotes 1, 2 or 3,
n denotes 0, 1 or 2,
p denotes 0, 1, 2, 3 or 4,
and pharmaceutically usable salts, tautomers and stereoisomers thereof, including mixtures thereof in all ratios.

The meanings and in particular the preferred meanings are the same as indicated in the case of the compounds of the formula I.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxyide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyland monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, maleate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an agueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically usable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and pharmaceutically usable salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-compound solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or as well as pharmaceutically usable salts, tautomers and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts, tautomers and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts, tautomers and stereoisomers thereof, including mixtures thereof in all ratios, and an effective amount of a further medicament active compound in dissolved or lyophilised form.

Use

The invention relates to the compounds of the formula I for use for the treatment of cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The invention relates to the use of compounds of the formula I for the preparation of a medicament for the treatment of cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease.

The invention relates to a method for the treatment of a mammal suffering from a disease selected from cancer, septic shock, primary open angle glaucoma (POAG), hyperplasia, rheumatoid arthritis, psoriasis, atherosclerosis, retinopathy, osteoarthritis, endometriosis, chronic inflammation and/or neurodegenerative diseases, such as Alzheimer's disease, where the method comprises the administration of a therapeutically effective amount of a compound of the formula I to a mammal.

The invention furthermore relates to the compounds of the formula I for use for the treatment of cancer, septic shock, primary open angle glaucoma (POAG), hyperplasia, atherosclerosis, retinopathy, osteoarthritis, endometriosis, chronic inflammation, neurodegenerative diseases, rheumatoid arthritis (RA), systemic lupus erythematosus (SLE), Sjorgren's syndrome, Aicardi-Goutiéres syndrome chilblain lupus, retinal vasculopathy, cerebral leukodystrophy (RVCL), systemic sclerosis, myositis, psoriasis, chronic obstructive pulmonary disease (CPD), inflammatory bowel disease (IBD), obesity, insulin resistance, type 2 diabetes (NIDDM) and/or metabolic syndrome The present compounds are suitable as pharmaceutical active compounds for mammals, in particular for humans, in the treatment and combating of cancer diseases and inflammatory diseases.

The host or patient can belong to any mammalian species, for example a primate species, particularly humans; rodents, including mice, rats and hamsters; rabbits; horses, cows, dogs, cats, etc. Animal models are of interest for experimental investigations, providing a model for the treatment of a human disease.

The susceptibility of a particular cell to treatment with the compounds according to the invention can be determined by in vitro tests. Typically, a culture of the cell is combined with a compound according to the invention at various concentrations for a period of time which is sufficient to make it possible for the active agents, such as anti-IgM, to induce a cell response, such as expression of a surface marker, usually between about one hour and one week. In vitro testing can be carried out using cultivated cells from blood or a biopsy sample. The amount of expressed surface marker is assessed by flow cytometry using specific antibodies which recognise the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

The present invention encompasses the use of the compounds of the formula I and/or physiologically acceptable salts, tautomers and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Likewise encompassed is the use of the compounds of the formula I and/or physiologically acceptable salts, tautomers and solvates thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the cancer disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, a-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamineplatinum(II)]bis[diamine(chloro)platinum(II)] tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino-[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino] benzo-[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Test for the Inhibition of IKKε

IKKε—Kinase Assay (IKKepsilon)
Summary
The kinase assay is performed as 384-well flashplate assay (for example for Topcount measurement).
1 nM IKKε, 800 nM biotinylated IκKα(19-42) peptide (Biotin-C6-C6-GLKKERLLDDRHDSGLDSMKDEE) and 10 μM ATP (spiked with 0.3 μCi of $^{33}$P-ATP/well) are incubated at 30° C. for 2 hours in a total volume of 50 μl (10 mM MOPS, 10 mM Mg acetate, 0.1 mM EGTA, 1 mM dithiothreitol, 0.02% of Brij35, 0.1% of BSA, 0.1% of BioStab, pH 7.5) with or without test compound. The reaction is stopped using 25 μl of 200 mM EDTA. After 30 min at room temperature, the liquid is removed, and each well is washed three times with 100 μl of 0.9% sodium chloride solution. Non-specific reaction is determined in the presence of 3 μM MSC2119074 (BX-795). The radioactivity is measured using a Topcount (Perkin Elmer). The results (for example $IC_{50}$ values) are calculated using program tools provided by the IT Department (for example AssayExplorer, Symyx).

Test for the Inhibition of TBK1

Enzyme Test
Summary
The kinase assay is performed as 384-well flashplate assay (for example for Topcount measurement).
0.6 nM TANK binding kinase (TBK1), 800 nM biotinylated MELK-derived peptide (biotin-Ah-Ah-AKP-KGNKDYHLQTCCGSLAYRRR) and 10 μM ATP (spiked with 0.25 μCi of $^{33}$P-ATP/well) are incubated at 30° C. for 120 min in a total volume of 50 μl (10 mM MOPS, 10 mM Mg acetate, 0.1 mM EGTA, 1 mM DTT, 0.02% of Brij35, 0.1% of BSA, pH 7.5) with or without test compound. The reaction is stopped with 25 μl of 200 mM EDTA. After 30 min at room temperature, the liquid is removed, and each well is washed three times with 100 µl of 0.9% sodium chloride solution. Non-specific reaction is measured in the presence of 100 nM staurosporine. The radioactivity is measured in a Topcount (PerkinElmer). The results (for example $IC_{50}$ values) are calculated using program tools provided by the IT Department (for example Assay-Explorer, Symyx).

Cell Test

Dose response inhibition of phospho-IRF3 @ Ser 386 cell/MDAMB468/INH/PHOS/IMAG/pIRF3

1. Scope

Although TBK1 and IKKε are mainly known as key substances in the innate immune response, recent findings have indicated a role for TBK1 and IKKε in Ras-induced oncogenic transformation. TBK1 was identified as RalB effector in the Ras-like (Ral)-guanine nucleotide exchange factor (GEF) pathway that is required for Ras-induced transformation. TBK1 directly activates IRF3 which, on phosphorylation, homodimerises and translocates to the nucleus, where it activates processes associated with inflammation, immune regulation, cell survival and proliferation.

This assay has been developed in order to assess the efficacy/potency of TBK1/IKKε inhibitor compounds based on the immunocytochemical detection of nucleus-localised phospho-IRF3, a target directly downstream of TBK1. Treatment with polyinosine-polycytidylic acid (poly(I:C), a synthetic analogue of double-stranded RNA (dsRNA), a molecular pattern associated with viral infection and recognised by Toll-like receptor 3 (TLR3) is used to induce TBK1/IKKε activity and IRF3 phosphorylation at Ser386.

2. Assay Overview

Day 1: MDA-MB-468 cells are detached using HyQ-Tase, counted and sown into a 384-well plate with TC surface and clear bottom in a density of 10,000 cells per well in a total volume of 35 µl of complete medium. Alternatively, the cells are sown directly from frozen glass vials.

Day 2: The cells are pre-treated with inhibitor compounds for 1 h prior to poly(I:C) stimulation. After incubation for 2 h with poly(I:C), the cells are fixed in (para)formaldehyde (PFA) and permeabilised using methanol (MeOH). The cells are then blocked and incubated with an anti-pIRF3 antibody at 4° C. overnight.

Day 3: The primary antibody is washed off, an AlexaFluor488-conjugated secondary antibody is added, the cells are contrast-stained with propidium iodide, followed by image acquisition on an IMX ultra-high content reader.

3. Reagents, Materials

Cells: ATCC HTB 132, Burger Lab (MP-CB 2010-327 or MDA-MB-468/10)

Plating medium=culture medium:
RPMI 1640, Invitrogen #31870
10% of FCS, Invitrogen #10270-106
  2 mM Glutamax, Invitrogen #35050-038
1 mM sodium pyruvate, Invitrogen #11360
  1% of Pen/Strep
37° C., 5% of $CO_2$ Plates: 384-well bottom cell culture plates with black/clear bottom, Falcon #35 3962 or Greiner #781090

Subcultivation: HyQ-Tase, Thermo Scientific (HyClone) # SV30030.01

Other Reagents:
Poly(I:C) (LMW), Invitrogen # tlrl-picw (prepare 20 mg/ml stock solution in sterile PBS, denature 30 min 55° C. in a water bath, slowly cool to RT, store at −20° C. in aliquots)

Reference inhibitor: MSC2119074A-4=BX-795 (IC50: 200-800 nM)

Inhibitory control: 10 µM MSC2119074A-4=BX-795
Neutral control: 0.5% of DMSO a 10-point dose-response curve with MSC2119074A-4=BX-795 is included in each experiment Hepes, Merck #1.10110
PBS 1×DPBS, Invitrogen #14190
Formaldehyde (methanol-free, 16%, ultrapure EM grade), Polysciences #18814 (storage RT), final conc.: 4%
Methanol, Merck #1.06009.1011 (−20° C. pre-cooled)
Goat serum, PAA # B15-035 (storage 4° C., long term −20° C.), final conc.: 10%
BSA (IgG- and protease-free, 30%), US-Biological # A1317 (storage 4° C., long term −20° C.), final conc.: 2%
Tween 20 detergent, Calbiochem #655204 (storage RT), (prepare 10% stock solution in water; final conc.: 0.1%)
Anti-pIRF-3 rabbit mAb, Epitomics #2526-B (storage −20° C.), final conc.: 1:2000 in PBS/2% of BSA
Alexa Fluor goat-anti-rabbit-488, Invitrogen # A11034 or #A11008 (storage 4° C., dark), final conc.: 1:2000 in PBS/2% of BSA/0.1% of Tween
Propidium iodide (PI), Fluka #81845, 1 mg/ml in $H_2O$ (storage 4° C., dark), final conc.: 0.2 µg/ml 4. Sequence (1) Sow 10,000 cells/well/35µof complete RPMI +10% FCS into 384-well bottom cell culture plates with black/clear bottom, (2) Incubate for 2 h at room temperature on the bench, followed by further incubation for 22 h at 37° C., 5% of $CO_2$ and 90% RH.

(3) Treatment of the compound:
add 5 µof prediluted compounds, standard or control reagents (8-fold conc.);
Cmpd. dilution of DMSO stock solutions in 20 mM Hepes pH 7.2; final DMSO conc.: 0.5%;
Serial dilution of the cmpds. from 10 mM stock solution (Remp) 10 steps, 3.16-fold in DMSO: 30 µM, 9.49 µM, 3 µM, 0,3 µM, 0,095 µM, 0,03 µM, 0,0095 µM, 0.003 µM, 0.00095 µM;
Incubate for 60 minutes at 37° C., 5% of $CO_2$ and 90% rH.

(4) Stimulation treatment:
add 10 µl of poly(I:C) to all wells except for unstimulated controls so that a final concentration of 100 µg/ml is achieved (stock solution 20 mg/ml →1:40 in PBS) (5-fold conc.);
Incubate for 120 minutes at 37° C., 5% of $CO_2$ and 90% RH.

(5) Completely remove supernatant by suction.
(6) Fix cells:
add 100 µl of 4% paraformaldehyde in PBS;
Incubate for 15 minutes at RT.
(7) Wash 3x with 80 µl of PBS (Tecan powerwasher), completely aspirate supernatant, Put plate on ice.
(8) Permeabilize cells:
quickly add 100 µl of MeOH at −20° C. (pre-cool reservoir);
Incubate for 10 minutes at RT or 4° C.,
(9) Wash once with 80 µl of PBS (Tecan powerwasher), completely remove supernatant by suction.
(10) Block non-specific binding:
add 30 µl of 10% goat serum in PBS/2% of BSA;
Shake on Multidrop Combi (17 seconds);
Incubate for 60 minutes at 37° C.
(11) Completely remove supernatant by suction.
(12) Primary staining:
add 25 µl of primary antibody diluted 1:2000 in PBS/2% BSA;
Shake on Multidrop Combi (17 seconds);
incubate overnight at 4° C.,

(13) Wash 3x with 80 μl of PBS (Tecan powerwasher), completely remove supernatant by suction,

(14) Secondary staining and nuclear staining:
add 25 pl of secondary antibody (1:2000) and 0.2 μg/ml of propidium iodide in PBS / 2% BSA / 0.1% Tween;
Shake on Multidrop Combi (17 seconds); Incubate for 75 minutes at 37° C.

(15) Wash 3x with 80 μl of PBS (Tecan powerwasher), completely remove supernatant by suction,

(16) Dispense 80 μl of PBS into all wells.

(17) Seal plates with transparent adhesive seal,

(18) Image acquisition on IMX Ultra (Metaexpress 3.1. scan settings TBK__10x$_{pin}$8).

(19) Image analysis (Metaexpress 3.1. <cell scoring>, TBK1 cell scoring).

(20) Data analysis and reporting using Assay Explorer.

HPLC/HPLC-MS Conditions

HPLC/MS conditions A

Column: Chromolith Performance ROD RP-18e, 100×3 mm$^2$

Gradient: A:B=99:1 to 0:100 in 3.5 min
Flow rate: 2.0 ml/min
Eluent A: water+0.05% of formic acid
Eluent B: acetonitrile+0.04% of formic acid
Wavelength: 220 nm
Mass spectroscopy: positive mode HPLC/MS conditions B Column: Chromolith Performance ROD RP-18e, 50×4.6 mm$^2$ Gradient: A:B=96:4 to 0:100 in 2.8 min
Flow rate: 2.40 ml/min
Eluent A: water+0.05% of formic acid
Eluent B: acetonitrile+0.04% of formic acid
Wavelength: 220 nm
Mass spectroscopy: positive mode HPLC/MS conditions C Column: Chromolith Performance ROD RP-18e, 100×3 mm$^2$ Gradient: A:B=99:1 to 0:100 in 1.8 min
Flow rate: 2.0 ml/min
Eluent A: water+0.05% of formic acid
Eluent B: acetonitrile+0.04% of formic acid
Wavelength: 220 nm
Mass spectroscopy: positive mode

EXAMPLE 1

The preparation of 5-(1H-pyrrolo[2,3-b]pyridin-3-yl)-2-tetrahydropyran-4-yloxybenzonitrile ("A1") is carried out analogously to the following scheme:

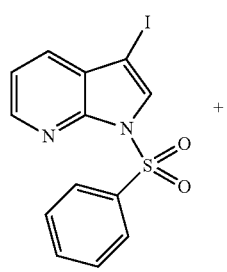

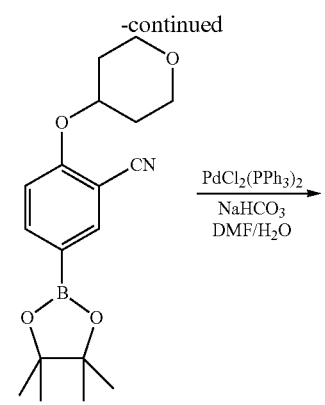

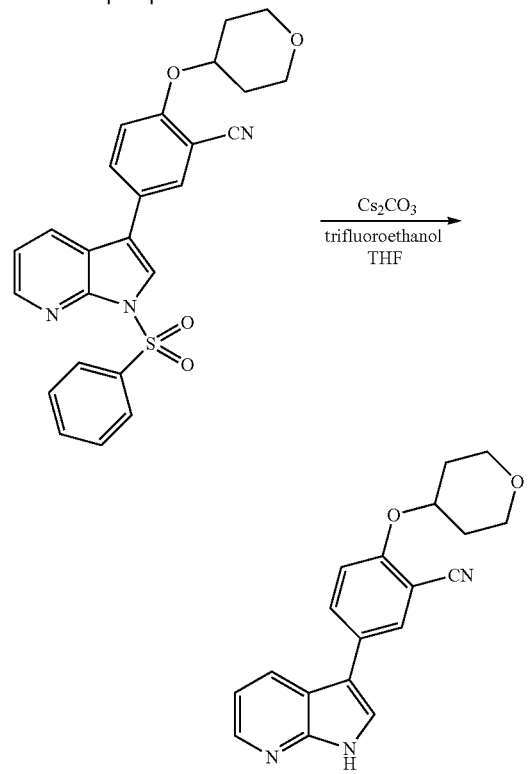

A suspension, kept under nitrogen, of 384 mg (1.00 mmol) of 1-(benzenesulfonyl)-3-iodopyrrolo[2,3-b]pyridine, 362 mg (1.10 mmol) of 2-tetrahydropyran-4-yloxy-5-(4,4,5,5-tetramethyl-1,3,2-dioxaborolan-2-yl)benzonitrile (preparation described in WO 2011/046970) and 101 mg (1.2 mmol) of sodium hydrogencarbonate in 2 ml of DMF and 1 ml of water is warmed to 40° C. with stirring. 14.0 mg (0.02 mmol) of bis(triphenylphosphine)palladium(II) chloride are then added. The reaction mixture is heated to 80° C. and stirred at this temperature for 18 hours. The reaction mixture is cooled to room temperature, and water is added. The precipitate formed is filtered off with suction, washed with water and dried in vacuo: 1-(benzenesulfonyl)-3-(3-methyl-4-tetrahydropyran-4-yloxyphenyl)pyrrolo[2,3-b]pyridine as grey powder; HPLC/MS (B): 2.47 min, [M+H] 460.

8 ml of 2,2,2-trifluoroethanol and 928 mg (2.85 mmol) of caesium carbonate are added to a suspension of 436 mg (0.95 mmol) of 1-(benzenesulfonyl)-3-(3-methyl-4-tetrahydropyran-4-yloxyphenyl)pyrrolo[2,3-b]pyridine in 8 ml of THF. The reaction mixture is stirred at 80° C. for 7 hours, cooled to room temperature and partitioned between THF and saturated sodium chloride solution. The organic phase is dried over sodium sulfate and evaporated. The residue is chromatographed on a silica-gel column with cyclohexane/ethyl acetate as eluent: 5-(1H-pyrrolo[2,3-b]pyridin-3-yl)-2-tetrahydropyran-4-yloxybenzonitrile as colourless crystals; HPLC/MS (B): 1.92 min, [M+H] 320; $^1$H NMR (400 MHz, DMSO-d$_6$) δ [ppm]=11.94 (s, 1H), 8.28 (m, 2H), 8.03 (d, J=2.3, 1H), 7.98 (dd, J=8.8, 2.4, 1H), 7.92 (d, J=2.2, 1H), 7.41 (d, J=8.9, 1H), 7.16 (dd, J=7.9, 4.8, 1H), 4.84 (tt, J=7.8, 3.8, 1H), 3.88 (m, 2H), 3.55 (ddd, J=11.5, 8.3, 3.1, 2H), 2.02 (m, 2H), 1.68 (m, 2H).

The following are obtained analogously:

5-(4-methoxy-1H-pyrrolo[2,3-b]pyridin-3-yl)-2-tetrahydropyran-4-yloxybenzonitrile ("A2")

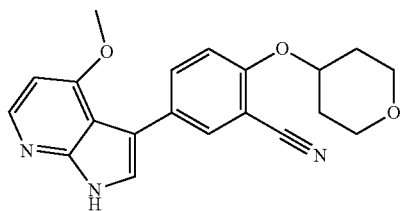 [SMILES: COc1ccnc2[nH]cc(-c3ccc(OC4CCOCC4)c(C#N)c3)c12]

starting from 1-(benzenesulfonyl)-3-iodo-4-methoxypyrrolo[2,3-b]pyridine (preparation described in WO2011/008915);

HPLC/MS (A): 1.85 min, [M+H] 350;

5-(6-methoxy-1H-pyrrolo[2,3-b]pyridin-3-yl)-2-tetrahydropyran-4-yloxybenzonitrile ("A3")

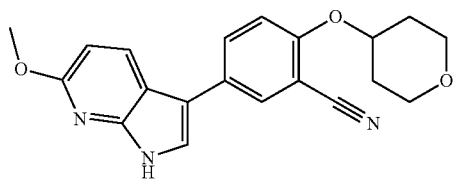 [SMILES: COc1ccc2c(-c3ccc(OC4CCOCC4)c(C#N)c3)c[nH]c2n1]

starting from 1-(benzenesulfonyl)-3-iodo-6-methoxypyrrolo[2,3-b]pyridine; HPLC/MS (A): 2.71 min, [M+H] 350.

EXAMPLE 2

The preparation of 5-[5-(1-methylpyrazol-4-yl)-1H-pyrrolo[2,3-b]pyridin-3-yl]-2-tetrahydropyran-4-yloxybenzonitrile ("A4") is carried out analogously to the following scheme:

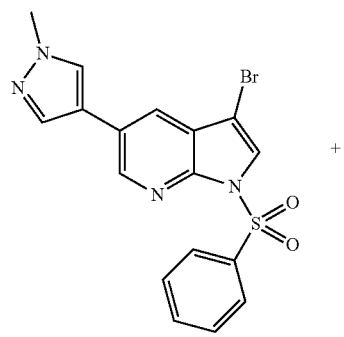

+

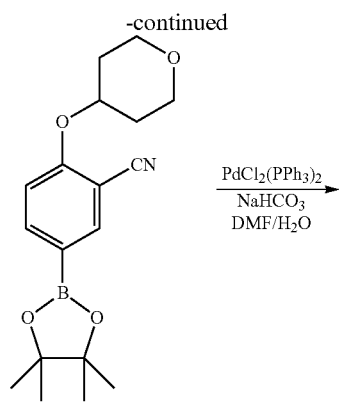

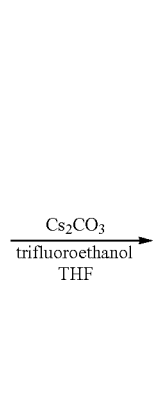

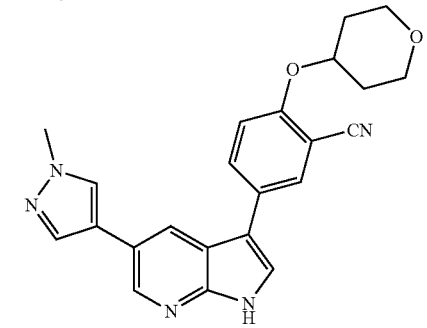

Starting from 1-(benzenesulfonyl)-3-bromo-5-(1-methylpyrazol-4-yl)pyrrolo[2,3-*pyridine (synthesis described in WO 2009/054941), the compound 515-(1-methylpyrazol-4-yl)-1H-pyrrolo[2,3-b]pyridin-3-yl]-2-tetrahydropyran-4-yloxybenzonitrile is prepared analogously to Example 1; slightly yellow crystals; HPLC/MS (B):

1.92 min, [M+H] 400;

$^1$H NMR (500 MHz, DMSO-d$_6$) δ [ppm]=11.91 (d, J=1.7, 1H), 8.53 (d, J=2.0, 1H), 8.35 (d, J=1.8, 1H), 8.23 (s, 1H), 8.06 (d, J=2.3, 1H), 8.03 (dd, J=8.8, 2.3, 1H), 7.97 (s, 1H), 7.90 (d, J=2.6, 1H), 7.41 (d, J=8.9, 1H), 4.85 (tt, J=7.7, 3.7, 1H), 3.89 (m, 5H), 3.56 (ddd, J=11.4, 8.3, 3.1, 2H), 2.03 (m, 2H), 1.70 (m, 2H).

EXAMPLE 3

The preparation of 5-(5-bromo-1H-pyrrolo[2,3-b]pyridin-3-yl)-2-tetrahydropyran-4-yl-oxy-benzonitrile ("A5") is carried out analogously to the following scheme:

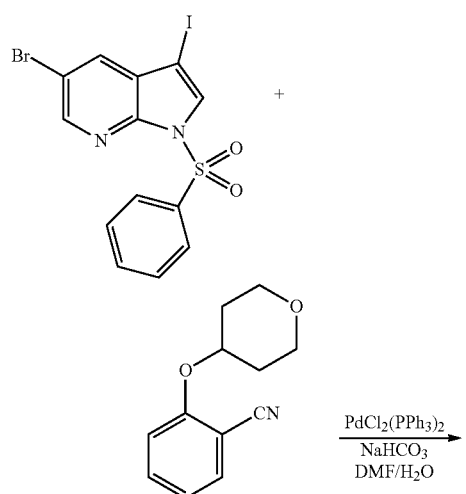

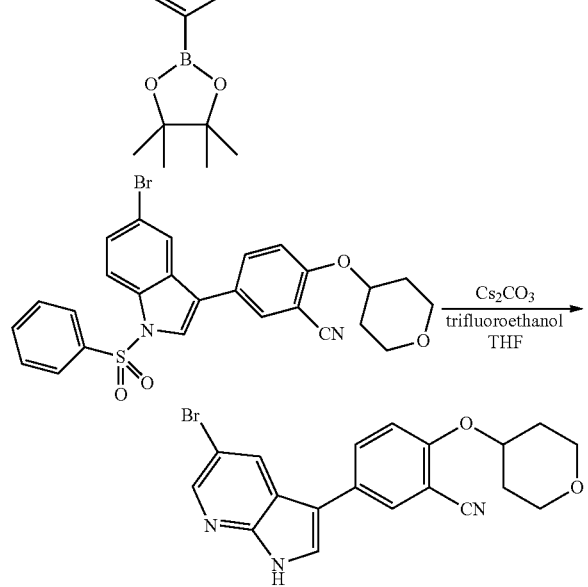

A suspension, kept under nitrogen, of 4.63 g (10.0 mmol) of 1-(benzenesulfonyl)-5-bromo-3-iodopyrrolo[2,3-b]pyridine, 3.62 g (11.0 mmol) of 2-tetrahydropyran-4-yloxy-5-(4,4,5,5-tetramethyl-1,3,2-dioxaborolan-2yl)benzonitrile and 1.01 g (12.0 mmol) of sodium hydrogencarbonate in 20 ml of DMF and 10 ml of water is warmed to 40° C. with stirring. 140 mg (0.20 mmol) of bis(triphenylphosphine)palladium(II) chloride are then added. The reaction mixture is heated to 80° C. and stirred at this temperature for 18 hours. The reaction mixture is cooled to room temperature, and water is added. The precipitate formed is filtered off with suction, washed with water and dried in vacuo: 5-[1-(benzenesulfonyl)-5-bromopyrrolo-[2,3-b]pyridin-3-yl]-2-tetrahydropyran-4-yloxybenzonitrile as pale-grey crystals; HPLC/MS (A): 3.32 min, [M+H] 538/540;

$^1$H NMR (400 MHz, DMSO-d$_6$) δ [ppm]=8.57 (d, J=2.1, 1H), 8.53 (d, J=2.1, 1H), 8.37 (s, 1H), 8.19 (d, J=2.3, 1H), 8.16 (d, J=7.3, 2H), 8.05 (dd, J=8.8, 2.4, 1H), 7.75 (m, 1H), 7.65 (t, J=7.8, 2H), 7.44 (d, J=9.0, 1H), 4.90 (dt, J=11.7, 3.9, 1H), 3.88 (m, 2H), 3.56 (ddd, J=11.4, 8.2, 3.2, 3H), 2.03 (m, 2H), 1.69 (dtd, J=12.1, 8.1, 3.8, 2H).

4 ml of 2,2,2-trifluoroethanol and 438 mg (1.35 mmol) of caesium carbonate are added to a suspension of 241 mg (0.45 mmol) of 5-[1-(benzenesulfonyl)-5-bromopyrrolo-[2,3-b]pyridin-3-yl]-2-tetrahydropyran-4-yloxybenzonitrile in 4 ml of THF. The reaction mixture is stirred at 80° C. for 3 hours, cooled to room temperature and partitioned between THF and saturated sodium chloride solution. The organic phase is dried over sodium sulfate and evaporated. The residue is chromatographed on a silica-gel column with cyclohexane/ethyl acetate as eluent: 5-(5-bromo-1H-pyrrolo[2,3-b]pyridin-3-yl)-2-tetrahydropyran-4-yloxybenzonitrile as colourless crystals; HPLC/MS (B): 2.32 min, [M+H] 398/400;

$^1$H NMR (400 MHz, DMSO-d$_6$) δ [ppm]=12.20 (s, 1H), 8.51 (d, J=2.1, 1H), 8.34 (d, J=2.1, 1H), 8.07 (d, J=2.3, 1H), 8.00 (s, 1H), 7.98 (dd, J=8.9, 2.4, 1H), 7.40 (d, J=8.9, 1H), 4.85 (tt, J=7.6, 3.7, 1H), 3.89 (m, 2H), 3.56 (ddd, J=11.4, 8.3, 3.1, 2H), 2.03 (m, 2H), 1.69 (dtd, J=12.2, 8.1, 3.8, 2H).

EXAMPLE 4

The preparation of 5-[5-(4-cyanophenyl)-1H-pyrrolo[2,3-b]pyridin-3-yl]-2-tetrahydropyran-4-yloxybenzonitrile ("A6") is carried out analogously to the following scheme:

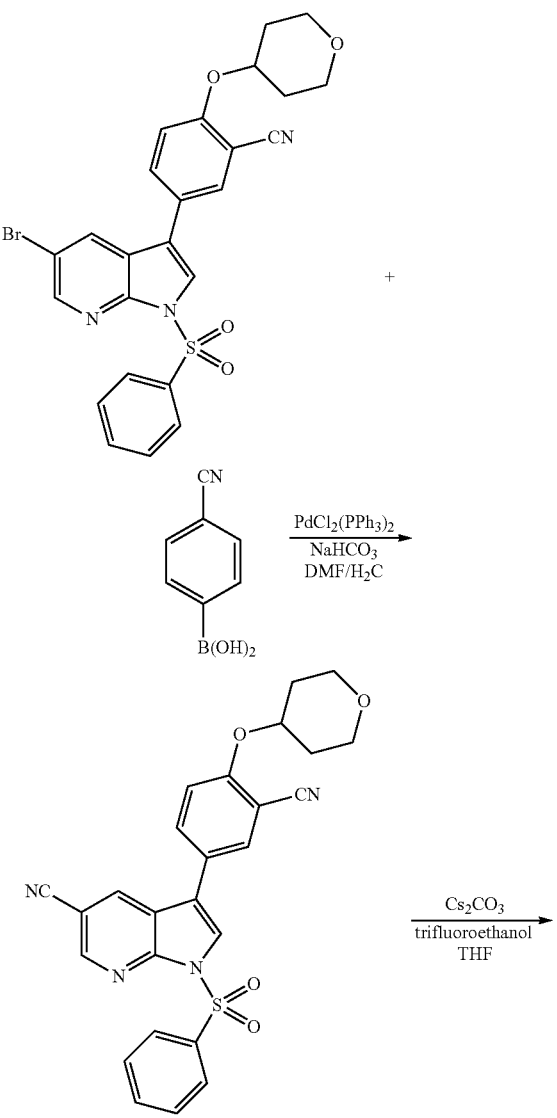

-continued

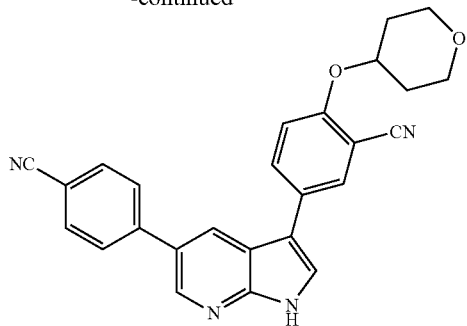

A suspension, kept under nitrogen, of 538 mg (1.00 mmol) of 5-[1-(benzenesulfonyl)-5-bromopyrrolo[2,3-b]pyridin-3-yl]-2-tetrahydropyran-4-yloxybenzonitrile, 162 mg (1.10 mmol) of 4-cyanophenylboronic acid and 101 mg (1.20 mmol) of sodium hydrogencarbonate in 2 ml of DMF and 1 ml of water is warmed to 40° C. with stirring. 14 mg (0.02 mmol) of bis(triphenylphosphine)palladium(II) chloride are then added. The reaction mixture is heated to 80° C. and stirred at this temperature for 4 days. The reaction mixture is cooled to room temperature and partitioned between water and dichloromethane. The organic phase is dried over sodium sulfate and evaporated. The residue is chromatographed on a silica-gel column with cyclohexane/ethyl acetate: 5-[1-(benzenesulfonyl)-5-(4-cyanophenyl)pyrrolo[2,3-b]-pyridin-3-yl]-2-tetrahydropyran-4-yloxybenzonitrile as colourless crystals; HPLC/MS (A): 3.55 min, [M+H] 561.

4 ml of 2,2,2-trifluoroethanol and 439 mg (1.35 mmol) of caesium carbonate are added to a suspension of 252 mg (0.45 mmol) of 5-[1-(benzenesulfonyl)-5-(4-cyanophenyl)pyrrolo[2,3-b]pyridin-3-yl]-2-tetrahydropyran-4-yloxybenzonitrile in 4 ml of THF. The reaction mixture is stirred at 80° C. for 3 hours, cooled to room temperature and partitioned between THF and saturated sodium chloride solution. The organic phase is dried over sodium sulfate and evaporated. The residue is chromatographed on a silica-gel column with cyclohexane/ethyl acetate as eluent: 5-[5-(4-cyanophenyl)-1H-pyrrolo[2,3-b]pyridin-3-yl]-2-tetrahydropyran-4-yloxybenzonitrile as colourless crystals; HPLC/MS (B): 2.31 min, [M+H] 421;

$^1$H NMR (500 MHz, DMSO-$d_6$) δ [ppm]=12.15 (s, 1H), 8.66 (d, J=2.1, 1H), 8.56 (d, J=2.1, 1H), 8.14 (d, J=2.3, 1H), 8.08 (dd, J=8.8, 2.3, 1H), 8.04 (d, J=8.5, 2H), 8.00 (s, 1H), 7.95 (d, J=8.5, 2H), 7.42 (d, J=8.9, 1H), 4.85 (tt, J=7.8, 3.8, 1H), 3.89 (m, 2H), 3.56 (ddd, J=11.4, 8.3, 3.1, 2H), 2.03 (m, 2H), 1.69 (dtd, J=12.2, 8.1, 3.8, 2H).

The following are prepared analogously:
5-[5-[1-(2-morpholinoethyl)pyrazol-4-yl]-1H-pyrrolo[2,3-b]pyridin-3-yl]-2-tetrahydropyran-4-yloxybenzonitrile ("A7")

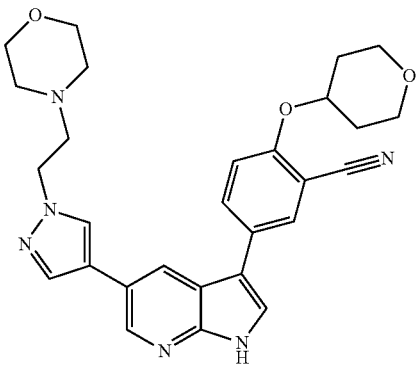 [SMILES: N#Cc1cc(-c2c[nH]c3ncc(-c4cnn(CCN5CCOCC5)c4)cc23)ccc1OC1CCOCC1]

starting from 4-[2-[4-(4,4,5,5-tetramethyl-1,3,2-dioxaborolan-2-yl)pyrazol-1-yl]ethyl]-morpholine;
HPLC/MS (B): 1.55 min, [M+H] 499;
5-[5-(4-morpholinophenyl)-1H-pyrrolo[2,3-b]pyridin-3-yl]-2-tetrahydropyran-4-yloxybenzonitrile ("A8")

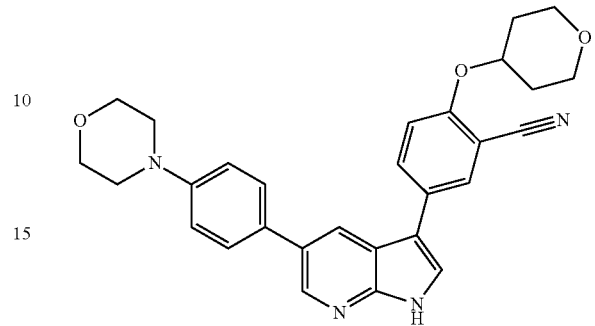

starting from 4-[4-(4,4,5,5-tetramethyl-1,3,2-dioxaborolan-2-yl)phenyl]morpholine; HPLC/MS (B): 2.26 min, [M+H] 481;
5-[5-[1-(2-pyrrolidin-1-ylethyl)pyrazol-4-yl]-1H-pyrrolo[2,3-b]pyridin-3-yl]-2-tetrahydropyran-4-yloxybenzonitrile ("A9")

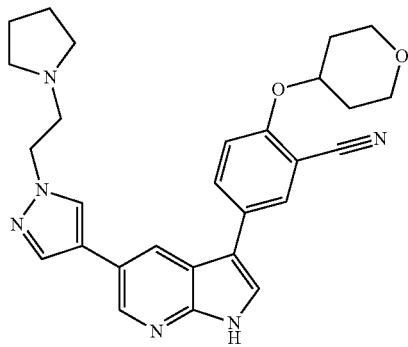 [SMILES: N#Cc1cc(-c2c[nH]c3ncc(-c4cnn(CCN5CCCC5)c4)cc23)ccc1OC1CCOCC1]

starting from 1-(2-pyrrolidin-1-ylethyl)-4-(4,4,5,5-tetramethyl-1,3,2-dioxaborolan-2-yl)-1H-pyrazole;
HPLC/MS (A): 1.83 min, [M+H] 483;
5-[5-[1-(2-methoxyethyl)pyrazol-4-yl]-1H-pyrrolo[2,3-b]pyridin-3-yl]-2-tetrahydropyran-4-yloxybenzonitrile ("A10")

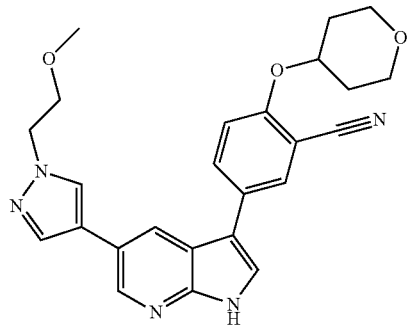 [SMILES: COCCn1cc(-c2cnc3[nH]cc(-c4ccc(OC5CCOCC5)c(C#N)c4)c3c2)cn1]

starting from 1-(2-methoxyethyl)-4-(4,4,5,5-tetramethyl-1,3,2-dioxaborolan-2-yl)-1H-pyrazole;
HPLC/MS (A): 2.30 min, [M+H] 444;

$^1$H NMR (400 MHz, DMSO-$d_6$) δ [ppm] 11.90 (s, 1H), 8.54 (d, J=2.0, 1H), 8.36 (d, J=2.0, 1H), 8.25 (s, 1H), 8.07 (d, J=2.3, 1H), 8.03 (dd, J=8.7, 2.3, 1H), 8.00 (s, 1H), 7.90 (s, 1H), 7.41 (d, J=8.9, 1H), 4.85 (tt, J=7.8, 3.8, 1H), 4.29 (t, J=5.4, 2H), 3.89 (m, 2H), 3.74 (t, J=5.4, 2H), 3.56 (ddd, J=11.4, 8.3, 3.1, 2H), 3.26 (s, 3H), 2.03 (m, 2H), 1.70 (dtd, J=12.3, 8.1, 3.9, 2H).

EXAMPLE 5

The preparation of 5-[2-methyl-5-(1-methylpyrazol-4-yl)-1H-pyrrolo[2,3-b]pyridin-3-yl]-2-tetrahydropyran-4-yloxy-benzonitrile ("A11") is carried out analogously to the following scheme:

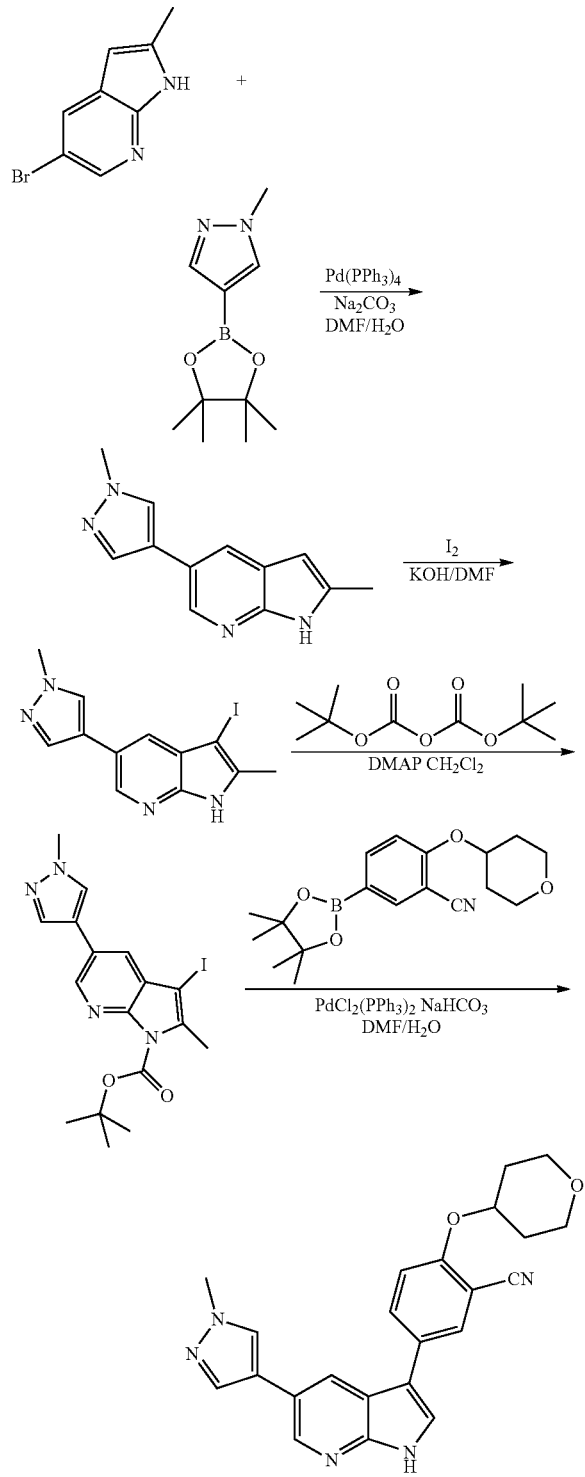

A solution of 3.18 g (30.0 mmol) of sodium carbonate in 15 ml of water is added to a solution, kept under nitrogen, of 2.11 g (10.0 mmol) of 5-bromo-2-methyl-1H-pyrrolo[2,3-b]pyridine and 3.54 g (17.0 mmol) of pinacolyl 1-methyl-1H-pyrazole-4-boronate in 30 ml of DMF. The mixture is heated to 80° C., 462 mg (0.40 mmol) of tetrakis(triphenylphosphine) palladium are added, and the mixture is stirred at 80° C. for 18 hours. The reaction mixture is cooled to room temperature, and 50 ml of water are added. The precipitate formed is filtered off with suction, washed with water and dried in vacuo: 2-methyl-5-(1-methylpyrazol-4-yl)-1H-pyrrolo[2,3-b]-pyridine as grey solid; HPLC/MS (A): 1.68 min, [M+H] 213.

1.12 g (20.0 mmol) of potassium hydroxide (as powder) are added to a suspension of 1.70 g (8.00 mmol) of 2-methyl-5-(1-methylpyrazol-4-yl)-1H-pyrrolo[2,3-b]pyridine in 8 ml of DMF, and a solution of 2.03 g (8.00 mmol) of iodine in 8 ml of DMF is subsequently added dropwise. The reaction mixture is stirred at room temperature for 30 minutes and subsequently partitioned between ethyl acetate and aqueous dilute sodium hydrogensulfite solution. The insoluble components are filtered off with suction and dried in vacuo: 3-iodo-2-methyl-5-(1-methylpyrazol-4-yl)-1H-pyrrolo[2,3-b]pyridine as grey powder; HPLC/MS (A): 2.45 min, [M+H] 339. Further product is isolated from the organic phase after drying over sodium sulfate and evaporation.

82.1 mg (0.67 mmol) of 4-(dimethylamino)pyridine and subsequently a solution of 2.20 g (10.1 mmol) of di-tert-butyl dicarbonate in 7 ml of dichloromethane are added dropwise to a suspension of 2.27 g (6.72 mmol) of 3-iodo-2-methyl-5-(1-methylpyrazol-4-yl)-1H-pyrrolo[2,3-b]pyridine in 14 ml of dichloromethane. The reaction mixture is stirred at room temperature for 30 minutes and subsequently washed twice with saturated sodium thiosulfate solution and once with water. The organic phase is dried over sodium sulfate and evaporated. The residue is chromatographed on a silica-gel column with cyclohexane/ethyl acetate as eluent: tert-butyl 3-iodo-2-methyl-5-(1-methylpyrazol-4-yl)pyrrolo[2,3-b]pyridine-1-carboxylate as colourless crystals; HPLC/MS (A): 3.35 min, [M+H] 439.

A solution, kept under nitrogen, of 285 mg (0.65 mmol) of tert-butyl 3-iodo-2-methyl-5-(1-methylpyrazol-4-yl)pyrrolo[2,3-b]pyridine-1-carboxylate, 213 mg (0.65 mmol) of 2-tetrahydropyran-4-yloxy-5-(4,4,5,5-tetramethyl-1,3,2-dioxaborolan-2-yl)benzonitrile and 4.56 mg (6.5 μmol) of bis(triphenylphosphine)palladium(II) chloride in 2 ml of DMF is heated to 80° C. After addition of 65.5 mg (0.78 mmol) of sodium hydrogencarbonate and 1 ml of water, the reaction mixture is stirred at 80° C. for 18 hours. The reaction mixture is cooled to room temperature and partitioned between water and dichloromethane. The organic phase is dried over sodium sulfate and evaporated. The residue is chromatographed on a silica-gel column with ethyl acetate/methanol as eluent: 5-[2-methyl-5-(1-methylpyrazol-4-yl)-1H-pyrrolo[2,3-b]-pyridin-3-yl]-2-tetrahydropyran-4-yloxybenzonitrile as pale-yellow crystals; HPLC/MS (A): 2.45 min, [M+H] 414.

$^1$H NMR (400 MHz, DMSO-d$_6$) δ [ppm]=11.71 (s, 1H), 8.42 (d, J=2.0, 1H), 8.15 (s, 1H), 7.96 (d, J=2.0, 1H), 7.89 (d, J=0.7, 1H), 7.79 (d, J=2.2, 1H), 7.76 (dd, J=8.7, 2.3, 1H), 7.44 (d, J=8.8, 1H), 4.85 (tt, J=7.8, 3.8, 1H), 3.90 (m, 5H), 3.56 (ddd, J=11.5, 8.4, 3.1, 2H), 2.46 (s, 3H), 2.05 (m, 2H), 1.71 (dtd, J=12.3, 8.2, 3.8, 2H).

EXAMPLE 6

The preparation of 5-[5-(1-piperidin-4-yl-1H-pyrazol-4-yl)-1H-pyrrolo[2,3-b]pyridin-3-yl]-2-(tetrahydropyran-4-yloxy)benzonitrile ("A12") is carried out analogously to the following scheme:

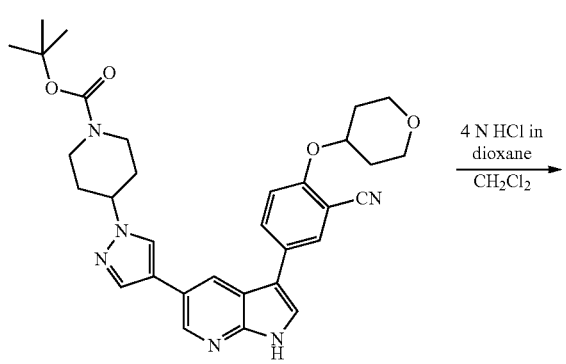

0.4 ml of a 0.4 N solution of hydrogen chloride in dioxane is added to a solution of 96.7 mg (0.17 mmol) of tert-butyl 4-(4-{3-[3-cyano-4-(tetrahydropyran-4-yloxy)phenyl]-1H-pyrrolo[2,3-b]pyridin-5-yl}pyrazol-1-yl)piperidine-1-carboxylate (prepared from tert-butyl 4-[4-(4,4,5,5-tetramethyl-1,3,2-dioxaborolan-2-yl)pyrazol-1-yl]piperidine-1-carboxylate) in 1.6 ml of dichloromethane. The reaction mixture is left at room temperature for 16 hours and subsequently partitioned between dichloromethane and saturated sodium carbonate solution. The organic phase is dried over sodium sulfate and evaporated: 5-[5-(1-piperidin-4-yl-1H-pyrazol-4-yl)-1H-pyrrolo-[2,3-b]pyridin-3-yl]-2-(tetrahydropyran-4-yloxy)benzonitrile as pale-yellow powder: HPLC/MS (B): 1.56 min, [M+H] 469;

$^1$H NMR (400 MHz, DMSO-d$_6$) δ [ppm]=11.94 (s, 1H), 8.59 (d, J=2.0, 1H), 8.41 (d, J=2.0, 1H), 8.36 (s, 1H), 8.11 (d, J=2.2, 1H), 8.08 (dd, J=8.7, 2.3, 1H), 8.02 (s, 1H), 7.93 (s, 1H), 7.45 (d, J=8.9, 1H), 4.89 (m, 1H), 4.25 (ddd, J=11.6, 7.5, 4.1, 1H), 3.93 (m, 2H), 3.60 (m, 2H), 3.10 (d, J=12.3, 2H), 2.66 (m, 2H), 2.06 (m, 5H), 1.88 (m, 2H), 1.74 (dtd, J=12.3, 8.2, 3.8, 2H).

EXAMPLE 7

The preparation of 2-(1-methylpiperidin-4-yloxy)-5-[5-(1-methyl-1H-pyrazol-4-yl)-1H-pyrrolo[2,3-b]pyridin-3-yl]benzonitrile ("A13") and of 5-(5-bromo-1H-pyrrolo[2,3-b]-pyridin-3-yl)-2-(cyclopropylmethoxy)benzonitrile ("A14") is carried out analogously to the following scheme:

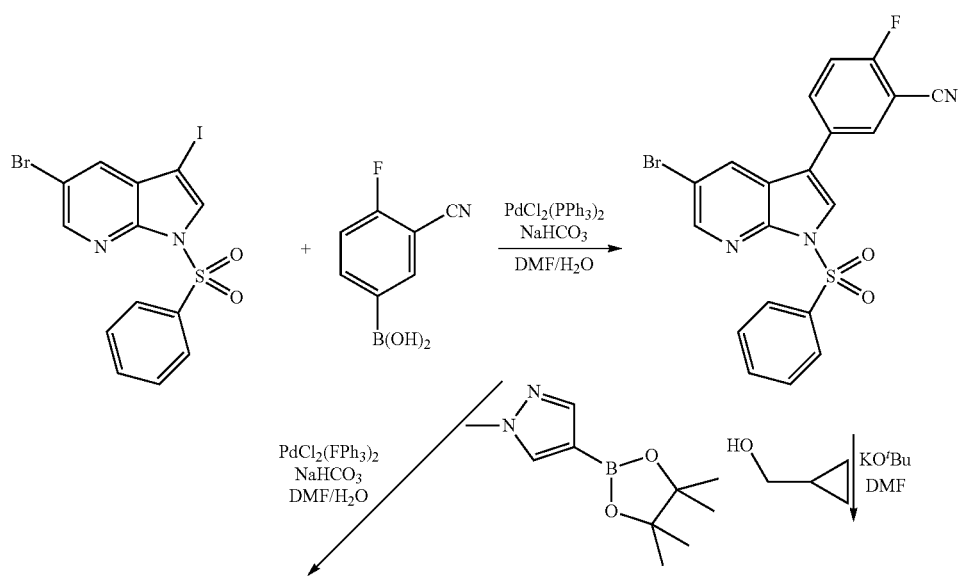

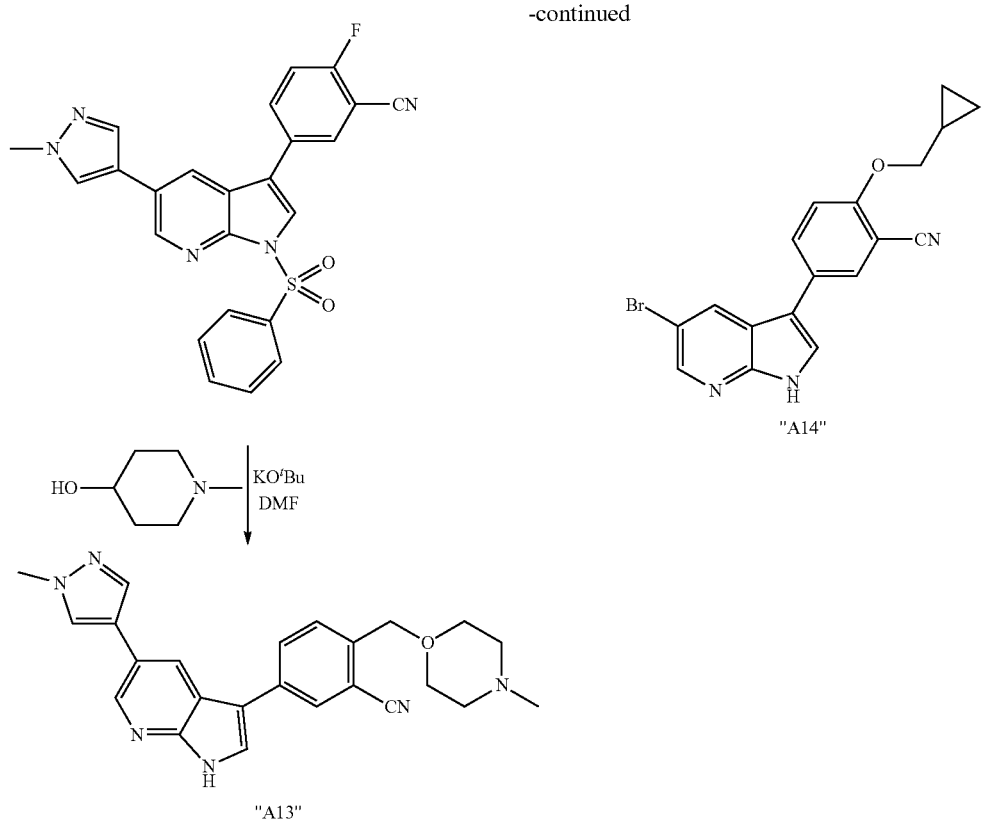

A suspension, kept under nitrogen, of 4.63 g (10.0 mmol) of 1-(benzenesulfonyl)-5-bromo-3-iodopyrrolo[2,3-b]pyridine, 1.81 g (11.0 mmol) of (3-cyano-4-fluorophenyl)boronic acid and 1.01 g (12.0 mmol) of sodium hydrogencarbonate in 20 ml of DMF and 10 ml of water is warmed to 40° C. with stirring. 140 mg (0.20 mmol) of bis(triphenylphosphine)palladium(II) chloride are then added. The reaction mixture is heated to 80° C. and stirred at this temperature for 18 hours. The reaction mixture is cooled to room temperature, and water is added. The precipitate formed is filtered off with suction, washed with water and dried in vacuo: 5-[1-(benzenesulfonyl)-5-bromo-pyrrolo[2,3-b]pyridin-3-yl]-2-fluorobenzonitrile as pale-brown powder; HPLC/MS (B): 2.77 min, [M+H] 456/458.

269 mg (2.39 mmol of potassium tert-butoxide and a suspension of 299 mg (0.67 mmol) of 5-[1-(benzenesulfonyl)-5-bromopyrrolo[2,3-b]pyridin-3-yl]-2-fluorobenzonitrile in 1.6 ml of DMF are added successively with external ice-cooling to a solution, kept under nitrogen, of 212 mg (2.93 mmol) of cyclopropylmethanol in 0.8 ml of DMF. The reaction mixture is stirred at room temperature for 20 hours and subsequently partitioned between water and dichloromethane. The organic phase is dried over sodium sulfate and evaporated. The residue is chromatographed on a silica-gel column with cyclohexane/ethyl acetate: 5-(5-bromo-1H-pyrrolo[2,3-b]pyridin-3-yl)-2-(cyclopropylmethoxy)benzonitrile ("A14") as colourless crystals; HPLC/MS (B): 2.32 min, [M+H] 398/400.

A suspension, kept under nitrogen, of 2.28 g (5.00 mmol) of 5-[1-(benzenesulfonyl)-5-bromopyrrolo[2,3-b]pyridin-3-yl]-2-fluorobenzonitrile, 1.14 g (5.50 mmol) of 1-methyl-4-(4,4,5,5-tetramethyl-1,3,2-dioxaborolan-2-yl)-1H-pyrazole and 504 mg (6.00 mmol) of sodium hydrogencarbonate in 10 ml of DMF and 5 ml of water is warmed to 40° C. with stirring. 70 mg (0.10 mmol) of bis(triphenylphosphine)palladium(II) chloride are then added. The reaction mixture is heated to 80° C. and stirred at this temperature for 20 hours. The reaction mixture is cooled to room temperature, and water is added. The precipitate formed is filtered off with suction, washed with water and chromatographed on a silica-gel column with cyclohexane/ethyl acetate as eluent: 5-[1-(benzenesulfonyl)-5-(1-methylpyrazol-4-yl)pyrrolo[2,3-b]pyridin-3-yl]-2-fluoro-benzonitrile as pale-grey crystals; HPLC/MS (B): 2.45 min, [M+H] 458.

449 mg (4.00 mmol) of potassium tert-butoxide and 457 mg (1.00 mmol) of 5-[1-(benzenesulfonyl)-5-(1-methylpyrazol-4-yl)pyrrolo[2,3-b]pyridin-3-yl]-2-fluorobenzonitrile are added successively with external ice-cooling to a solution of 705 µl (6.00 mmol) of 1-methyl-4-piperidinol in 2 ml of DMF. The reaction mixture is stirred at room temperature for 4 days and subsequently partitioned between water and ethyl acetate. The organic phase is dried over sodium sulfate and evaporated. The residue is chromatographed on a silica-gel column with methanol/dichloromethane as eluent: 2-(1-methylpiperidin-4-yloxy)-5-[5-(1-methyl-1H-pyrazol-4-yl)-1H-pyrrolo-[2,3-b]pyridin-3-yl]benzonitrile ("A13") as pale-yellow crystals; HPLC/MS (A): 1.64 min, [M+H] 413;

$^1$H NMR (400 MHz, DMSO-d$_6$) δ [ppm]=11.90 (d, J=1.9, 1H), 8.53 (d, J=2.0, 1H), 8.35 (d, J=1.9, 1H), 8.23 (s, 1H), 8.04 (m, 2H), 8.01 (d, J=2.4, 1H), 7.89 (d, J=2.6, 1H), 7.36 (d, J=8.8, 1H), 4.65 (m, 1H), 3.89 (s, 3H), 2.61 (m, 2H), 2.28 (m, 2H), 2.20 (s, 3H), 1.97 (m, 2H), 1.76 (m, 2H).

EXAMPLE 8

The preparation of 5-[5-[1-(2-hydroxyethyl)pyrazol-4-yl]-1H-pyrrolo[2,3-b]pyridin-3-yl]-2-tetrahydropyran-4-yloxy-benzonitrile ("A15") is carried out analogously to the following scheme:

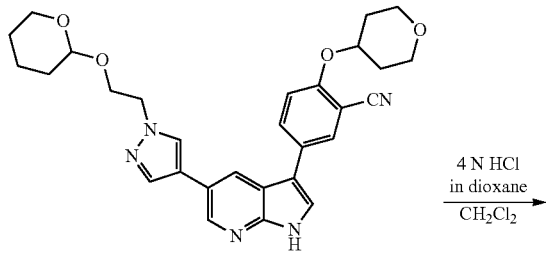

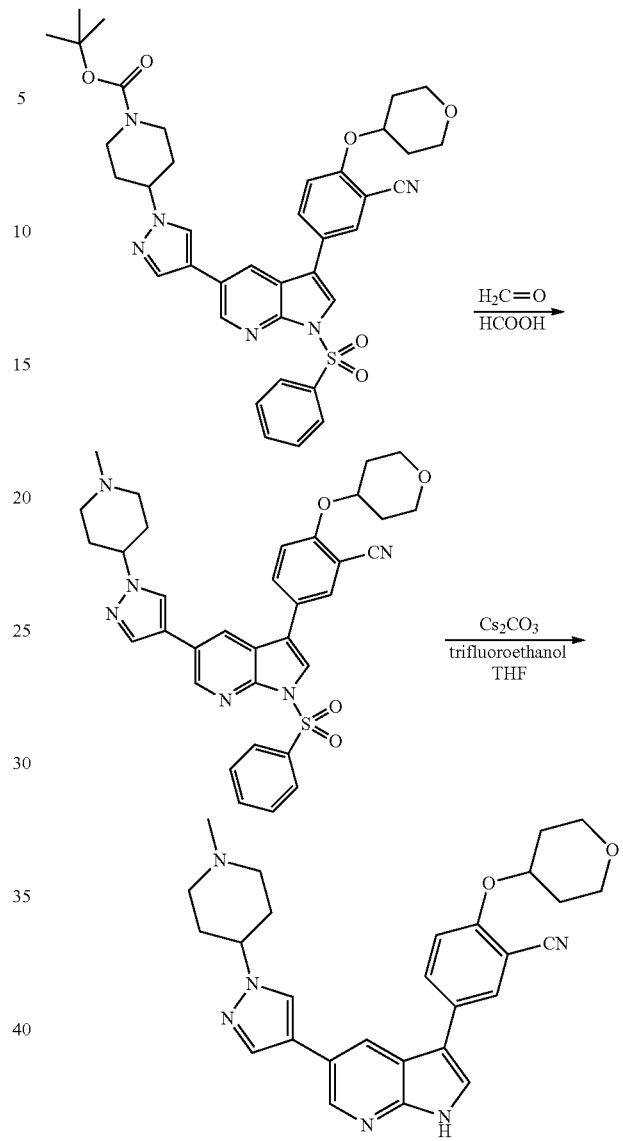

0.5 ml of a 0.4 N solution of hydrogen chloride in dioxane is added to a solution of 208 mg (0.405 mmol) of 2-(tetrahydropyran-4-yloxy)-5-(5-{1-[2-(tetrahydropyran-2-yloxy)ethyl]-1H-pyrazol-4-yl}-1H-pyrrolo[2,3-b]pyridin-3-yl)benzonitrile (prepared from 1-[2-(tetrahydropyran-2-yloxy)ethyl]-4-(4,4,5,5-tetramethyl-1,3,2-dioxaborolan-2-yl)-1H-pyrazole) in 7 ml of dichloromethane. The reaction mixture is left at room temperature for 30 minutes and subsequently partitioned between dichloromethane and saturated sodium carbonate solution. The organic phase is dried over sodium sulfate and evaporated: 5-[5-[1-(2-hydroxyethyl)pyrazol-4-yl]-1H-pyrrolo[2,3-b]pyridin-3-yl]-2-tetrahydropyran-4-yloxybenzonitrile as yellow powder: HPLC/MS (A): 1.83 min, [M+H] 430;

$^1$H NMR (400 MHz, DMSO-$d_6$) δ [ppm]=11.90 (d, J=2.2, 1H), 8.54 (d, J=2.0, 1H), 8.36 (d, J=1.9, 1H), 8.25 (s, 1H), 8.06 (d, J=2.2, 1H), 8.03 (dd, J=8.7, 2.3, 1H), 7.99 (s, 1H), 7.90 (d, J=2.7, 1H), 7.41 (d, J=8.9, 1H), 4.92 (s, 1H), 4.85 (ddd, J=11.8, 7.8, 3.9, 1H), 4.18 (t, J=5.7, 2H), 3.89 (m, 2H), 3.79 (t, J=5.6, 2H), 3.56 (m, 2H), 2.03 (m, 2H), 1.70 (dtd, J=12.3, 8.1, 3.8, 2H).

EXAMPLE 9

The preparation of 5-[5-[1-(1-methyl-4-piperidyl)pyrazol-4-yl]-1H-pyrrolo[2,3-b]pyridin-3-yl]-2-tetrahydropyran-4-yloxybenzonitrile ("A16") is carried out analogously to the following scheme:

0.07 ml of a 35% aqueous formaldehyde solution are added to a solution of 201 mg (0.28 mmol) of tert-butyl 4-(4-{1-benzenesulfonyl-3-[3-cyano-4-(tetrahydropyran-4-yloxy)phenyl]-1H-pyrrolo[2,3-b]pyridin-5-yl}pyrazol-1-yl)piperidine-1-carboxylate (prepared from tert-butyl 4-[4-(4,4,5,5-tetramethyl-1,3,2-dioxaborolan-2-yl)pyrazol-1-yl]piperidine-1-carboxylate) in 1.1 ml of formic acid. The reaction mixture is stirred at 80° C. for 4 hours and subsequently evaporated in vacuo. The residue is partitioned between 2 N NaOH and dichloromethane. The organic phase is dried over sodium sulfate and evaporated. The residue is chromatographed on a silica-gel column with dichloromethane/methanol as eluent: 5-{1-benzenesulfonyl-5-[1-(1-methylpiperidin-4-yl)-1H-pyrazol-4-yl]-1H-pyrrolo[2,3-b]pyridin-3-yl}-2-(tetrahydropyran-4-yloxy)benzonitrile as white powder; HPLC/MS (A): 2.17 min, [M+H] 623.

1.4 ml of 2,2,2-trifluoroethanol and 164 mg (0.51 mmol) of caesium carbonate are added to a solution of 105 mg (0.168 mmol) of 5-{1-benzenesulfonyl-5-[1-(1-methylpiperidin-4-yl)-1H-pyrazol-4-yl]-1H-pyrrolo[2,3-b]pyridin-3-yl}-2-(tetrahydropyran-4-yloxy)benzonitrile in 1.4 ml of THF, and the mixture is stirred at 80° C. for 3 hours. The reaction mixture is partitioned between THF and saturated sodium chloride solution. The organic phase is dried over sodium sulfate, evaporated, and the residue is chromatographed on a silica-gel column with dichloromethane/methanol as eluent: 5-[5-[1-(1-methyl-4-piperidyl)pyrazol-4-yl]-1H-pyrrolo[2,3-b]pyridin-3-yl]-2-tetrahydropyran-4-yloxybenzonitrile as colourless crystals; HPLC/MS (A): 1.83 min, [M+H] 483;

$^1$H NMR (400 MHz, DMSO-$d_6$) δ [ppm]=11.92 (d, J=1.7, 1H), 8.55 (d, J=2.0, 1H), 8.37 (d, J=1.9, 1H), 8.35 (s, 1H), 8.07 (d, J=2.3, 1H), 8.03 (dd, J=8.7, 2.4, 1H), 7.99 (d, J=0.5, 1H), 7.90 (d, J=2.5, 1H), 7.41 (d, J=8.9, 1H), 4.85 (tt, J=7.8, 3.8, 1H), 4.13 (td, J=10.0, 4.6, 1H), 3.89 (m, 2H), 3.56 (ddd, J=11.4, 8.3, 3.1, 2H), 2.87 (d, J=8.5, 2H), 2.22 (s, 3H), 2.03 (m, 8H), 1.69 (dtd, J=12.3, 8.2, 3.9, 2H).

EXAMPLE 10

The preparation of 5-[5-(4-methylpiperazin-1-yl)-1H-pyrrolo[2,3-b]pyridin-3-yl]-2-tetrahydropyran-4-yloxybenzonitrile ("A17") is carried out analogously to the following scheme:

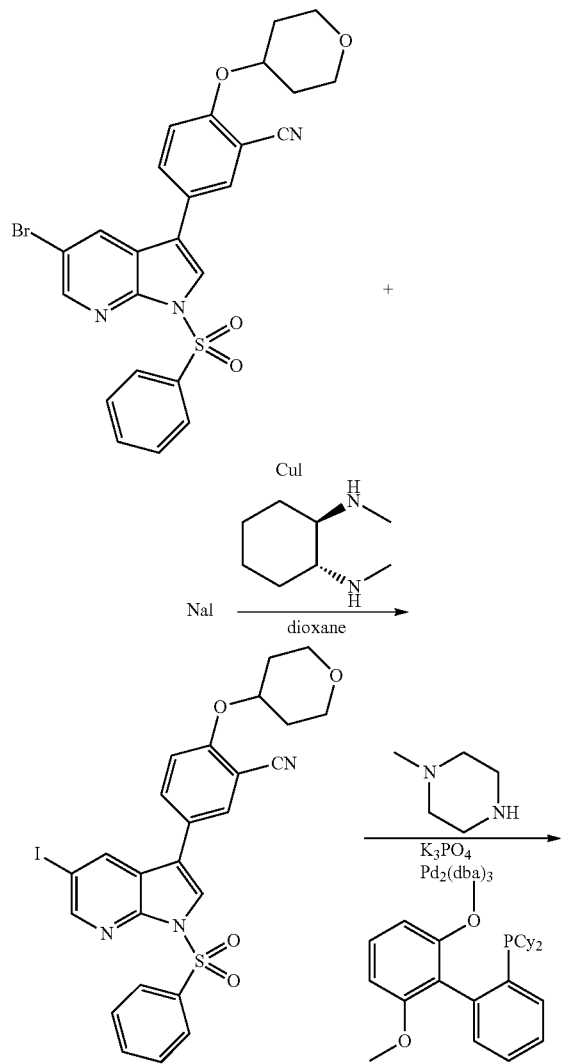

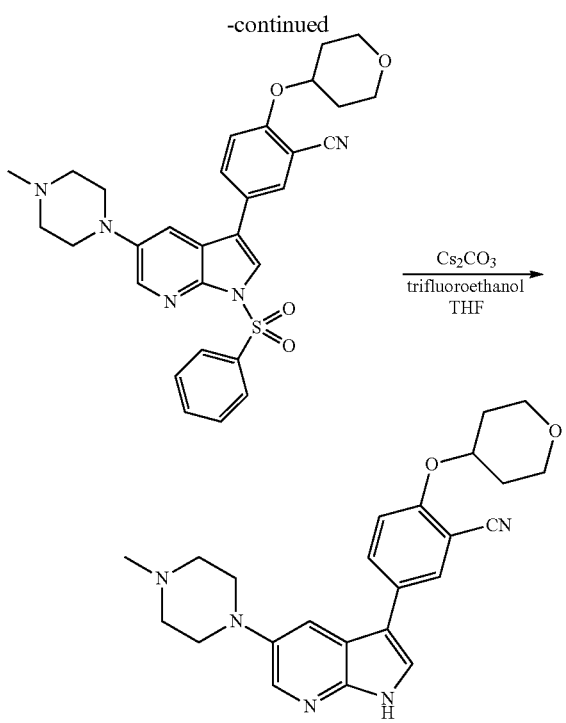

15 µl of trans-N,N'-dimethyl-1,2-cyclohexandiamine are added to a suspension, kept under nitrogen, of 538 mg (1.00 mmol) of 5-[1-(benzenesulfonyl)-5-bromopyrrolo-[2,3-b]pyridin-3-yl]-2-tetrahydropyran-4-yloxybenzonitrile, 315 mg (2.10 mmol) of sodium iodide and 9.5 mg (0.050) of copper(I) iodide in 2.0 ml of dioxane. The reaction mixture is stirred at 100° C. for 20 hours. The reaction mixture is cooled to room temperature and partitioned between water and dichloromethane. The organic phase is dried over sodium sulfate, evaporated, and the residue is chromatographed on a silicagel column with cyclohexane/ethyl acetate as eluent: 5-[1-(benzenesulfonyl)-5-iodopyrrolo[2,3-b]pyridin-3-yl]-2-tetrahydropyran-4-yloxybenzonitrile as colourless powder; HPLC/MS (A): 3.34 min, [M+H] 586.

A suspension, kept under nitrogen, of 385 mg (0.662 mmol) of 5-[1-(benzenesulfonyl)-5-iodopyrrolo[2,3-b]pyridin-3-yl]-2-tetrahydropyran-4-yloxybenzonitrile, 220 mg (1.04 mmol) of tripotassium phosphate, 0.124 ml (1.11 mmol) of 1-methylpiperazine, 24.3 mg (0.06 mmol) of 2-dicyclohexylphosphino-2',6'-dimethoxybiphenyl and 6.8 mg (0.007 mmol) of tris(dibenzylideneacetone)dipalladium in 1 ml of toluene is heated to 110° C. and stirred at this temperature for 4 days. The reaction mixture is partitioned between THF and saturated sodium chloride solution. The organic phase is dried over sodium sulfate and evaporated. The residue is chromatographed on a silica-gel column with methanol/ethyl acetate as eluent: 5-[1-(benzenesulfonyl)-5-(4-methylpiperazin-1-yl)pyrrolo[2,3-b]pyridin-3-yl]-2-tetrahydropyran-4-yloxybenzonitrile as yellow powder; HPLC/MS (A): 2.11 min, [M+H] 558.

0.3 ml of 2,2,2-trifluoroethanol and 25 mg (0.076 mmol) of caesium carbonate are added to a solution of 14 mg (0.025 mmol) of 5-[1-(benzenesulfonyl)-5-(4-methylpiperazin-1-yl)pyrrolo[2,3-b]pyridin-3-yl]-2-tetrahydropyran-4-yloxybenzonitrile in 0.3 ml of THF, and the mixture is stirred at 80°

C. for 3 hours. The reaction mixture is partitioned between THF and saturated sodium chloride solution. The organic phase is dried over sodium sulfate, evaporated, and the residue is chromatographed on a silicagel column with dichloromethane/methanol as eluent: 5-[5-(4-methylpiperazin-1-yl)-1H-pyrrolo[2,3-b]pyridin-3-yl]-2-tetrahydropyran-4-yloxybenzonitrile as pale-yellow powder; HPLC/MS (A): 1.71 min, [M+H] 418;

$^1$H NMR (500 MHz, DMSO-$d_6$) δ [ppm]=11.71 (s, 1H), 8.14 (d, J=2.4, 1H), 7.99 (d, J=2.3, 1H), 7.95 (dd, J=8.8, 2.3, 1H), 7.82 (d, J=2.6, 1H), 7.71 (s, 1H), 7.40 (d, J=8.9, 1H), 4.83 (tt, J=7.8, 3.8, 1H), 3.88 (m, 2H), 3.55 (ddd, J=11.4, 8.3, 3.1, 2H), 3.18 (bs, 3H), 2.6 (broad signal, 8H), 2.02 (m, 2H), 1.69 (dtd, J=12.3, 8.2, 3.8, 2H).

EXAMPLE 11

The preparation of

5-[5-[1-(4-piperidyl)pyrazol-4-yl]-1H-pyrrolo[2,3-b]pyridin-3-yl]-2-tetrahydropyran-4-yl-oxypyridine-3-carbonitrile ("A18"), 5-[5-[1-[1-(benzenesulfonyl)-4-piperidyl]pyrazol-4-yl]-1H-pyrrolo[2,3-b]pyridin-3-yl]-2-tetrahydropyran-4-yloxypyridine-3-carbonitrile ("A19") and 5-[5-[1-(1-methyl-4-piperidyl)pyrazol-4-yl]-1H-pyrrolo[2,3-b]pyridin-3-yl]-2-tetrahydropyran-4-yloxybenzonitrile ("A20")

is carried out analogously to the following scheme:

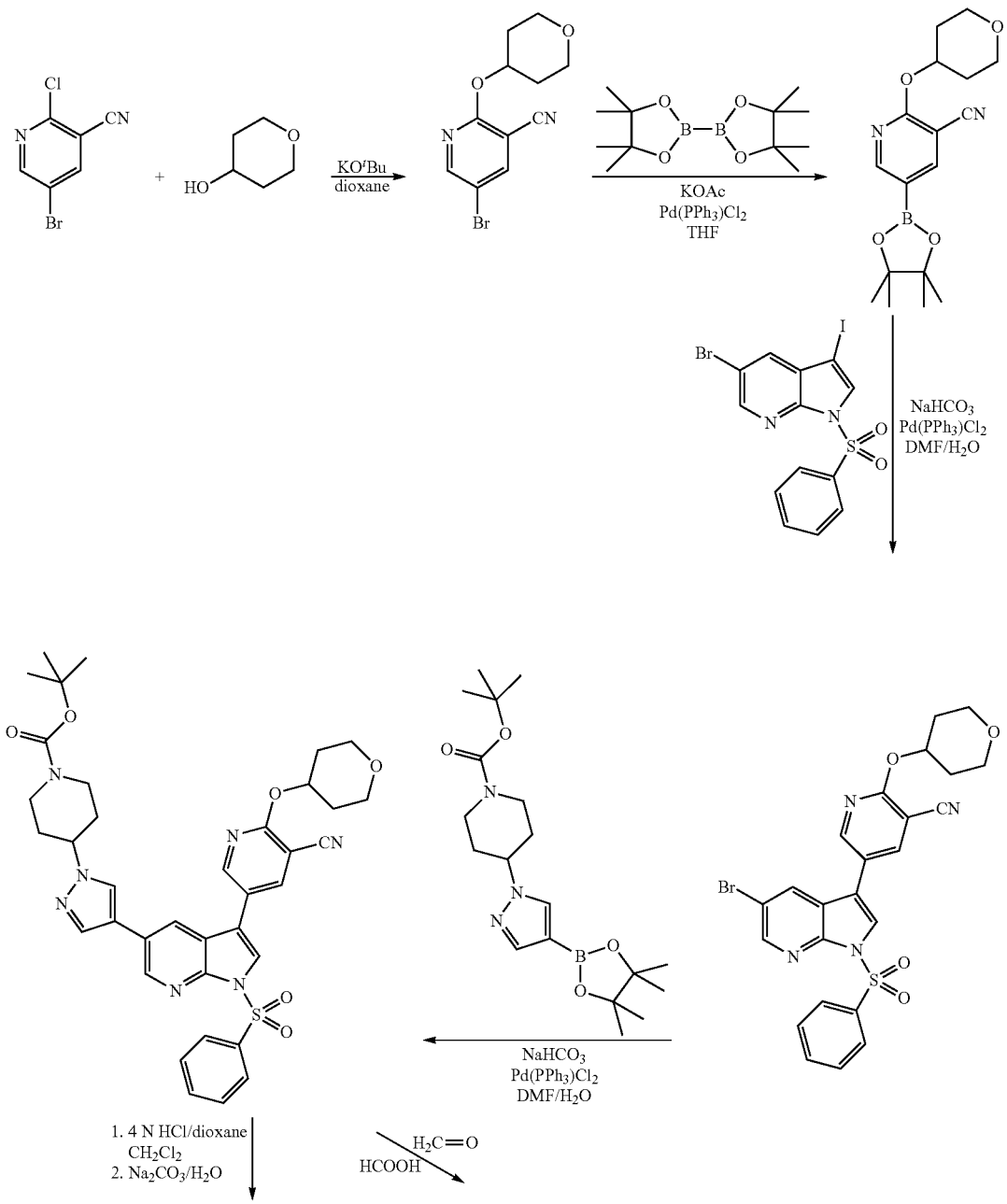

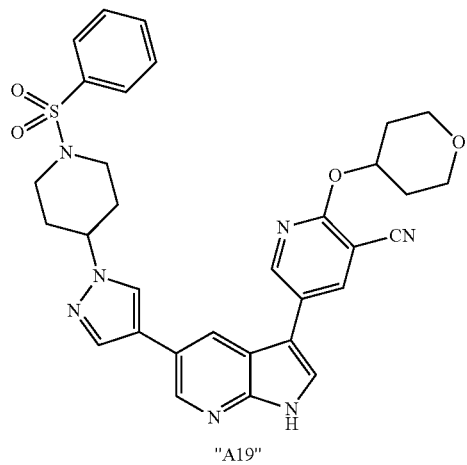

"A19"

+

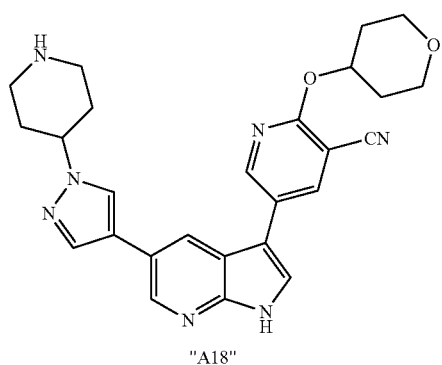

"A18"

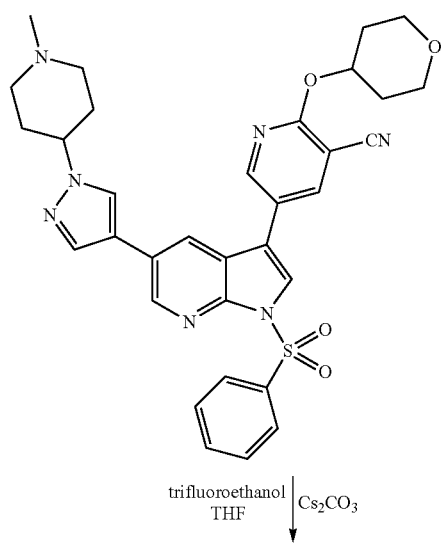

trifluoroethanol
THF | Cs₂CO₃

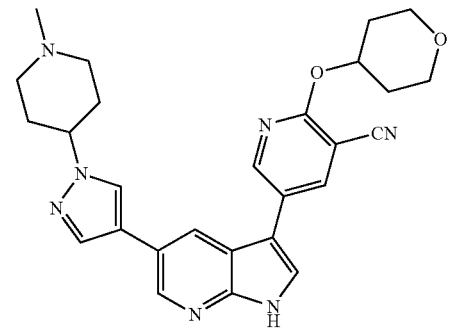

"A20"

2.55 g (22.7 mmol) of potassium tert-butoxide are added with external ice-cooling to a solution, kept under nitrogen, of 2.32 g (22.7 mmol) of tetrahydropyran-4-ol in 10 ml of dioxane. A solution of 2.47 g (11.4 mmol) of 5-bromo-2-chloronicotinonitrile in 10 ml of dioxane is then added dropwise to the suspension formed, and the reaction mixture is stirred at room temperature for 90 minutes. The reaction mixture is partitioned between water and dichloromethane. The organic phase is dried over sodium sulfate and evaporated. The residue is chromatographed on a silica-gel column with cyclohexane/ethyl acetate as eluent: 5-bromo-2-(tetrahydropyran-4-yloxy)nicotinonitrile as colourless crystals; HPLC/MS (B): 2.23 min, [M+H] 283/285.

1.56 g (15.9 mmol) of dry potassium acetate are added to a solution, kept under nitrogen, of 1.50 g (5.30 mmol) of 5-bromo-2-(tetrahydropyran-4-yloxy)nicotinonitrile and 1.75 g (6.89 mmol) of bis(pinacoloto)diboron in 10 ml of THF, and the mixture is stirred at 40° C. for 40 minutes. 74 mg (0.11 mmol) of bis(triphenylphosphine)palladium(II) chloride are subsequently added, and the reaction mixture is stirred at 80° C. for 16 hours. The reaction mixture is partitioned between water and dichloromethane. The organic phase is dried over sodium sulfate and evaporated. The residue is chromatographed on a silica-gel column with cyclohexane/ethyl acetate as eluent: 2-tetrahydropyran-4-yloxy-5-(4,4,5,5-tetramethyl-1,3,2-dioxaborolan-2-yl)pyridine-3-carbonitrile as yellow oil; HPLC/MS (A): 3.09 min, [M+H] 331.

¹H NMR (400 MHz, DMSO-d₆) δ [ppm]=8.59 (d, J=1.9, 1H), 8.30 (d, J=1.9, 1H), 5.40 (tt, J=8.3, 4.0, 1H), 3.85 (m, 2H), 3.54 (ddd, J=11.7, 8.8, 3.0, 2H), 2.03 (ddd, J=7.8, 3.8, 2.1, 2H), 1.70 (m, 2H), 1.30 (s, 12H).

A suspension, kept under nitrogen, of 1.11 g (2.41 mmol) of 1-(benzenesulfonyl)-5-bromo-3-iodopyrrolo[2,3-b]pyridine, 864 mg (2.65 mmol) of 2-tetrahydropyran-4-yloxy-5-(4,4,5,5-tetramethyl-1,3,2-dioxaborolan-2-yl)pyridine-3-carbonitrile and 243 mg (2.89 mmol) of sodium hydrogencarbonate in 5 ml of DMF and 2.5 ml of water is warmed to 40° C. with stirring. 34 mg (0.05 mmol) of bis(triphenylphosphine)palladium(II) chloride are then added.

The reaction mixture is heated to 80° C. and stirred at this temperature for 18 hours. The reaction mixture is cooled to room temperature, and water is added. The precipitate formed is filtered off with suction, washed with water and chromatographed on a silica-gel column with cyclohexane/ethyl acetate as eluent: 5-[1-(benzenesulfonyl)-5-bromopyrrolo[2, 3-b]pyridin-3-yl]-2-tetrahydropyran-4-yloxypyridine-3-carbonitrile as beige powder; HPLC/MS (A): 3.33 min, [M+H] 539/541.

A suspension, kept under nitrogen, of 696 mg (1.29 mmol) of 5-[1-(benzenesulfonyl)-5-bromopyrrolo[2,3-b]pyridin-3-yl]-2-tetrahydropyran-4-yloxypyridine-3-carbonitrile, 535 mg (1.42 mmol) of tert-butyl 4-[4-(4,4,5,5-tetramethyl-1,3, 2-dioxaborolan-2-yl)pyrazol-1-yl]piperidine-1-carboxylate and 130 mg (1.55 mmol) of sodium hydrogencarbonate in 2.6 ml of DMF and 1.3 ml of water is warmed to 40° C. with stirring. 18 mg (0.03 mmol) of bis(triphenylphosphine)palladium(II) chloride are then added. The reaction mixture is heated to 80° C. and stirred at this temperature for 4 days. The reaction mixture is cooled to room temperature and partitioned between water and dichloromethane. The organic phase is dried over sodium sulfate and evaporated. The residue is chromatographed on a silica-gel column with cyclohexane/ethyl acetate: tert-butyl 4-[4-[1-(benzenesulfonyl)-3-(5-cyano-6-tetrahydropyran-4-yloxy-3-pyridyl)pyrrolo[2,3-b]-pyridin-5-yl]pyrazol-1-yl]piperidine-1-carboxylate as yellowish foam; HPLC/MS (A): 3.37 min, [M+H] 710.

A 4 N solution of hydrogen chloride in dioxane is added to a solution of 397 mg (0.56 mmol) of tert-butyl 4-[4-[1-(benzenesulfonyl)-3-(5-cyano-6-tetrahydropyran-4-yloxy-3-pyridyl)pyrrolo[2,3-b]pyridin-5-yl]pyrazol-1-yl]piperidine-1-carboxylate in 5 ml of dichloromethane, and the mixture is stirred at room temperature for 4 days. The reaction mixture is partitioned between dichloromethane and saturated sodium carbonate solution. The organic phase is dried over sodium sulfate and evaporated. The residue is separated by preparative HPLC: 5-[5-[1[1-(benzenesulfonyl)-4-piperidyl]pyrazol-4-yl]-1H-pyrrolo[2,3-b]pyridin-3-yl]-2-tetrahydropyran-4-yloxypyridine-3-carbonitrile ("A19") as yellowish powder; HPLC/MS (A): 2.77 min, [M+H] 610;

$^1$H NMR (500 MHz, DMSO-d$_6$) δ [ppm]=12.00 (d, J=2.2, 1H), 8.89 (d, J=2.5, 1H), 8.62 (d, J=2.5, 1H), 8.55 (d, J=1.9, 1H), 8.42 (d, J=1.7, 1H), 8.36 (s, 1H), 8.02 (s, 1H), 7.98 (d, J=2.7, 1H), 7.80 (m, 2H), 7.75 (m, 1H), 7.68 (t, J=7.5, 2H), 5.38 (tt, J=8.3, 3.9, 1H), 4.25 (tt, J=11.1, 4.0, 1H), 3.90 (m, 2H), 3.77 (d, J=12.1, 2H), 3.56 (ddd, J=11.6, 8.9, 2.9, 2H), 2.54 (m, 2H), 2.17 (m, 2H), 2.04 (m, 4H), 1.75 (m, 2H); 5-[5-[1-(4-piperidyl)pyrazol-4-yl]-1H-pyrrolo[2,3-b]pyridin-3-yl]-2-tetrahydropyran-4-yloxypyridine-3-carbonitrile formate ("A18") as colourless powder; HPLC/MS (A): 1.81 min, [M+H] 470;

0.13 ml of a 35% aqueous formaldehyde solution are added to a solution of 396 mg (0.56 mmol) of tert-butyl 4-[4-[1-(benzenesulfonyl)-3-(5-cyano-6-tetrahydropyran-4-yloxy-3-pyridyl)pyrrolo[2,3-b]pyridin-5-yl]pyrazol-1-yl]piperidine-1-carboxylate in 2.2 ml of formic acid. The reaction mixture is stirred at 80° C. for 4 hours and subsequently evaporated in vacuo. The residue is partitioned between 2 N NaOH and dichloromethane. The organic phase is dried over sodium sulfate and evaporated. The residue is chromatographed on a silica-gel column with dichloromethane/methanol as eluent: 5-[1-(benzenesulfonyl)-5-[1-(1-methyl-4-piperidyl)pyrazol-4-yl]pyrrolo[2,3-b]pyridin-3-yl]-2-tetrahydropyran-4-yloxypyridine-3-carbonitrile as white powder; HPLC/MS (A): 2.21 min, [M+H] 624.

2.8 ml of 2,2,2-trifluoroethanol and 326 mg (1.00 mmol) of caesium carbonate are added to a solution of 208 mg (0.334 mmol) of 5-[1-(benzenesulfonyl)-5-[1-(1-methyl-4-piperidyl)pyrazol-4-yl]pyrrolo[2,3-b]pyridin-3-yl]-2-tetrahydropyran-4-yloxypyridine-3-carbonitrile in 2.8 ml of THF, and the mixture is stirred at 80° C. for 3 hours. The reaction mixture is partitioned between THF and saturated sodium chloride solution. The organic phase is dried over sodium sulfate, evaporated, and the residue is chromatographed on a silica-gel column with dichloromethane/methanol as eluent: 5-[5-[1-(1-methyl-4-piperidyl)pyrazol-4-yl]-1H-pyrrolo[2, 3-b]pyridin-3-yl]-2-tetrahydropyran-4-yloxybenzonitrile ("A20") as colourless crystals; HPLC/MS (B): 1.55 min, [M+H] 484;

$^1$H NMR (400 MHz, DMSO-d$_6$) δ [ppm]=12.00 (d, J=2.4, 1H), 8.90 (d, J=2.5, 1H), 8.63 (d, J=2.5, 1H), 8.57 (d, J=2.0, 1H), 8.44 (d, J=1.9, 1H), 8.39 (s, 1H), 8.03 (s, 1H), 7.98 (d, J=2.7, 1H), 5.38 (tt, J=8.3, 4.0, 1H), 4.16 (m, 1H), 3.90 (m, 2H), 3.56 (ddd, J=11.6, 8.8, 3.0, 2H), 2.93 (d, J=9.0, 2H), 2.27 (s, 3H), 2.17 (s, 2H), 2.06 (m, 6H), 1.75 (m, 2H).

EXAMPLE 12

The preparation of 5-[5-(2-morpholinoethoxy)-1H-pyrrolo[2,3-b]pyridin-3-yl]-2-tetrahydropyran-4-yloxybenzonitrile ("A21") is carried out analogously to the following scheme:

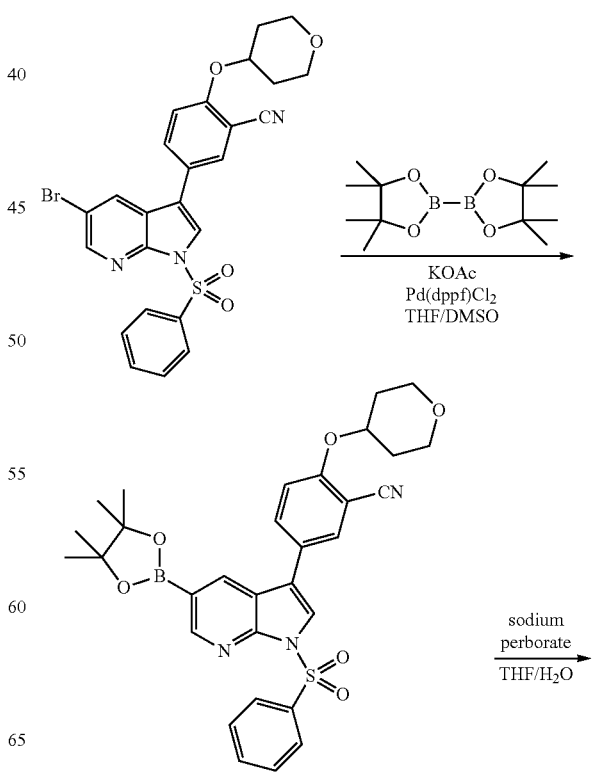

-continued

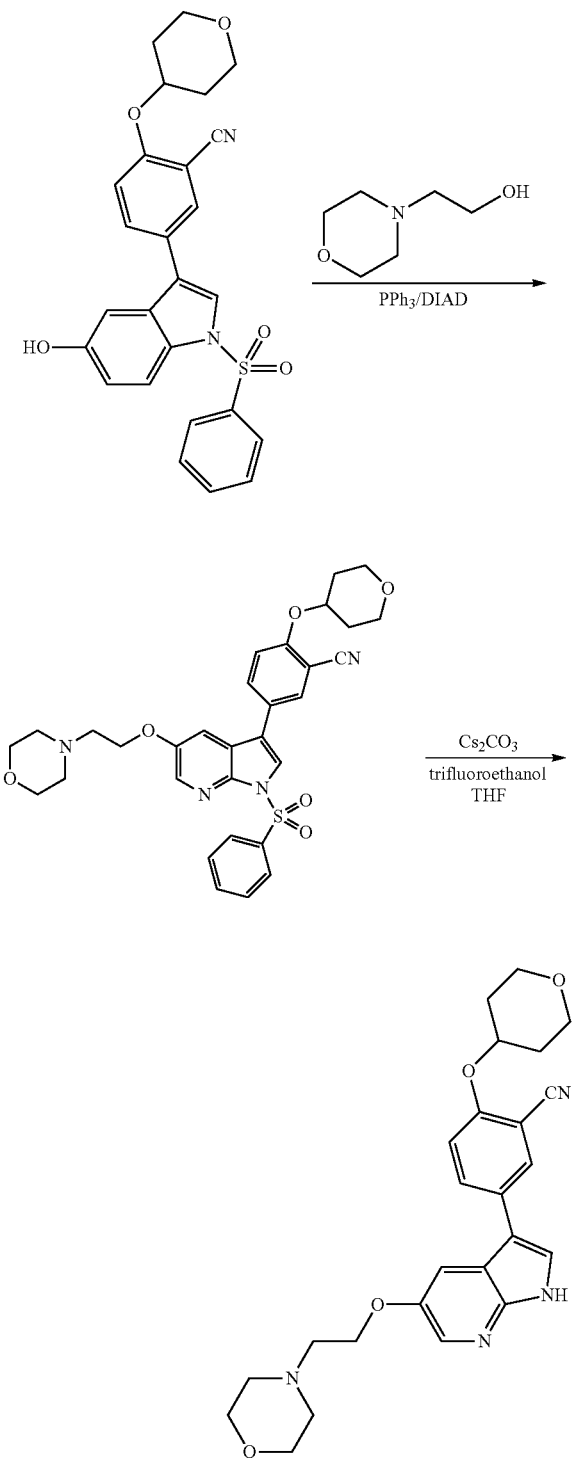

2 ml of DMSO and 393 mg (4.00 mmol of dry potassium acetate are added to a solution, kept under nitrogen, of 1.08 g (2.00 mmol) of 5-[1-(benzenesulfonyl)-5-bromopyrrolo[2,3-b]pyridin-3-yl]-2-tetrahydropyran-4-yloxybenzonitrile and 559 mg (2.20 mmol) of bis(pinacoloto)diboron in 4 ml of THF. 82 mg (0.10 mmol) of [1,1'-bis(diphenylphosphino) ferrocene]palladium(II) dichloride are subsequently added, and the reaction mixture is stirred at 80° C. for 20 hours. The reaction mixture is partitioned between water and dichloromethane. The organic phase is dried over sodium sulfate and evaporated. The residue is chromatographed on a silica-gel column with cyclohexane/ethyl acetate as eluent: 5-[1-(benzenesulfonyl)-5-(4,4,5,5-tetramethyl-1,3,2-dioxaborolan-2-yl)pyrrolo[2,3-b]pyridin-3-yl]-2-tetrahydropyran-4-yloxybenzonitrile as brown highly viscous oil; HPLC/MS (A): 3.50 min, [M+H] 586.

180 mg (1.17 mmol) of sodium perborate tetrahydrate and 1 ml of water are added to a suspension of 274 mg (0.468 mmol) of 5-[1-(benzenesulfonyl)-5-(4,4,5,5-tetramethyl-1,3,2-dioxaborolan-2-yl)pyrrolo[2,3-b]pyridin-3-yl]-2-tetrahydropyran-4-yloxybenzonitrile in 1 ml of THF. The mixture is stirred at room temperature for 20 hours, subsequently diluted with THF and filtered. The filtrate is evaporated in vacuo; the residue is taken up in water, and 0.5 ml of 1 N HCl is added. The precipitate formed is filtered off with suction, washed with water, dried in air and then chromatographed on a silica-gel column with cyclohexane/ethyl acetate as eluent: 5-[1-(benzenesulfonyl)-5-hydroxy-pyrrolo[2,3-b]pyridin-3-yl]-2-tetrahydropyran-4-yloxybenzonitrile as slightly yellow powder; HPLC/MS (A): 2.72 min, [M+H] 476.

88.5 mg (0.44 mmol) of diisopropyl azodicarboxylate are added dropwise to a solution of 139 mg (0.292 mmol) of 5-[1-(benzenesulfonyl)-5-hydroxypyrrolo[2,3-b]pyridin-3-yl]-2-tetrahydropyran-4-yloxybenzonitrile, 57 mg (0.44 mmol) of N-(2-hydroxyethyl)morpholine and 115 mg (0.44 mmol) of triphenylphosphine in 3 ml of THF. The reaction mixture is stirred at room temperature for 2 hours, evaporated and subsequently chromatographed on a silica-gel column with ethyl acetate/methanol as eluent: 5-[1-(benzenesulfonyl)-5-(2-morpholinoethoxy)pyrrolo[2,3-b]pyridin-3-yl]-2-tetrahydropyran-4-yloxybenzonitrile as white foam; HPLC/MS (A): 2.13 min, [M+H] 589.

1 ml of 2,2,2-trifluoroethanol and 207 mg (0.64 mmol) of caesium carbonate are added to a suspension of 125 mg (0.334 mmol) of 5-[1-(benzenesulfonyl)-5-(2-morpholinoethoxy)pyrrolo[2,3-b]pyridin-3-yl]-2-tetrahydropyran-4-yloxybenzonitrile in 1 ml of THF, and the mixture is stirred at 80° C. for 16 hours. The reaction mixture is evaporated, and the residue is chromatographed on a silica-gel column with dichloromethane/methanol as eluent: 5-[5-(2-morpholinoethoxy)-1H-pyrrolo[2,3-b]pyridin-3-yl]-2-tetrahydropyran-4-yloxybenzonitrile as slightly yellow powder; HPLC/MS (A): 1.75 min, [M+H] 449;
$^1$H NMR (500 MHz, DMSO-$d_6$) δ [ppm]=11.79 (d, J=1.7, 1H), 8.03 (d, J=2.6, 1H), 8.00 (d, J=2.3, 1H), 7.97 (dd, J=8.8, 2.4, 1H), 7.86 (d, J=2.7, 1H), 7.79 (d, J=2.5, 1H), 7.39 (d, J=8.9, 1H), 4.83 (tt, J=7.8, 3.8, 1H), 4.21 (t, J=5.8, 2H), 3.88 (m, 2H), 3.56 (m, 6H), 2.73 (t, J=5.7, 2H), 2.5 (m, 4H), 2.02 (m, 2H), 1.69 (dtd, J=12.3, 8.1, 3.8, 2H).

EXAMPLE 13

The preparation of 5-[5-[1-(4-piperidyl)triazol-4-yl]-1H-pyrrolo[2,3-b]pyridin-3-yl]-2-tetrahydropyran-4-yloxybenzonitrile ("A22") and 5-[5-[1-(1-methyl-4-piperidyl)triazol-4-yl]-1H-pyrrolo[2,3-b]pyridin-3-yl]-2-tetrahydropyran-4-yloxybenzonitrile ("A23") is carried out analogously to the following scheme:

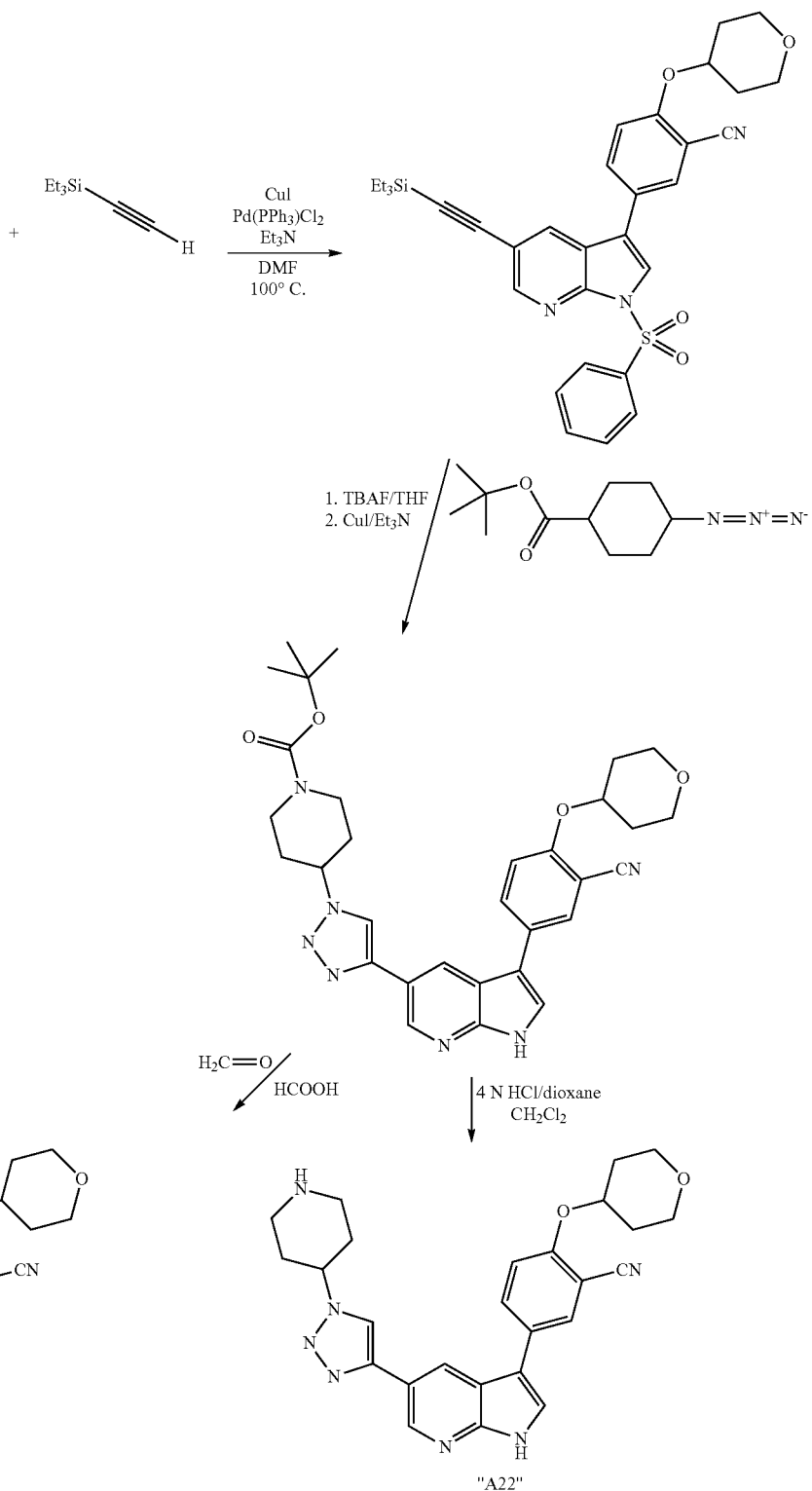

"A23"  "A22"

70.1 mg (0.10 mmol) of bis(triphenylphosphine)palladium (II) chloride, 5.7 mg (0.03 mmol) of copper(I) iodide, 416 μl (3.0 mmol) of triethylamine and 351 mg (2.50 mmol) of triethylsilylacetylene are added to a solution, kept under nitrogen, of 538 mg (1.00 mmol) of 5-[1-(benzenesulfonyl)-5-bromopyrrolo[2,3-b]pyridin-3-yl]-2-tetrahydropyran-4-yloxybenzonitrile in 5 ml of DMF. The reaction mixture is stirred at 100° C. for 18 hours. The mixture is cooled to room temperature and partitioned between water and dichloromethane. The organic phase is washed with 0.1 N HCl, dried over sodium sulfate and evaporated. The residue is taken up in tert-butyl methyl ether, the suspension is warmed and filtered off rapidly with suction. The filtrate is evaporated, and the residue is crystallised from cyclohexane: 5-[1-(benzenesulfonyl)-5-(2-triethylsilylethynyl)pyrrolo[2,3-b]pyridin-3-yl]-2-tetrahydropyran-4-yloxybenzonitrile as pale-grey powder; HPLC/MS (A): 4.08 min, [M+H] 598.

1 ml (1 mmol) of a 1 M solution of tetrabutylammonium fluoride in THF are added to a solution, kept under nitrogen, of 466 mg (0.779 mmol) of 5-[1-(benzenesulfonyl)-5-(2-triethylsilylethynyl)pyrrolo[2,3-b]pyridin-3-yl]-2-tetrahydropyran-4-yloxybenzonitrile in 5 ml of THF, and the solution is stirred at room temperature for 1 hour. 216 µl (1.56 mmol) of triethylamine, 211 mg (0.934 mmol) of tert-butyl 4-azidopiperidine-1-carboxylate and 7.4 mg (0.04 mmol) of copper(I) iodide are subsequently added. The reaction mixture is stirred at 80° C. for 18 hours and subsequently evaporated in vacuo. The residue is chromatographed on a silica-gel column with methanol/ethyl acetate as eluent: tert-butyl 4-[4-[3-(3-cyano-4-tetrahydropyran-4-yloxyphenyl)-1H-pyrrolo[2,3-b]pyridin-5-yl]triazol-1-yl]piperidine-1-carboxylate as cream-coloured solid; HPLC/MS (A): 2.77 min, [M+H] 570.

0.5 ml of a 0.4 N solution of hydrogen chloride in dioxane is added to a solution of 138 mg (0.24 mmol) of tert-butyl 4-[4-[3-(3-cyano-4-tetrahydropyran-4-yloxyphenyl)-1H-pyrrolo[2,3-b]pyridin-5-yl]triazol-1-yl]piperidine-1-carboxylate in 1 ml of dichloromethane, and the mixture is stirred at room temperature for 16 hours. The reaction mixture is diluted with dichloromethane. The precipitate formed is filtered off with suction, washed with acetone and dried in vacuo: 5-[5-[1-(4-piperidyl)triazol-4-yl]-1H-pyrrolo[2,3-b]pyridin-3-yl]-2-tetrahydropyran-4-yloxybenzonitrile hydrochloride as yellow solid: HPLC/MS (A): 1.77 min, [M+H] 470;

$^1$H NMR (500 MHz, DMSO-d$_6$) δ [ppm]=12.11 (d, J=1.8, 1H), 9.10 (d, J=9.9, 1H), 8.88 (d, J=9.8, 1H), 8.84 (s, 1H), 8.78 (s, 1H), 8.66 (d, J=1.6, 1H), 8.07 (d, J=2.3, 1H), 8.02 (dd, J=8.8, 2.3, 1H), 7.97 (d, J=2.6, 1H), 7.46 (d, J=9.0, 1H), 4.88 (m, 2H), 3.89 (m, 2H), 3.56 (ddd, J=11.4, 8.3, 3.1, 2H), 3.45 (d, J=13.0, 2H), 3.16 (q, J=12.3, 2H), 2.38 (m, 2H), 2.26 (m, 2H), 2.04 (m, 2H), 1.70 (dtd, J=12.3, 8.1, 3.8, 2H).

0.06 ml of a 35% aqueous formaldehyde solution are added to a solution of 138 mg (0.243 mmol) of tert-butyl 4-[4-[3-(3-cyano-4-tetrahydropyran-4-yloxyphenyl)-1H-pyrrolo[2,3-b]pyridin-5-yl]triazol-1-yl]piperidine-1-carboxylate in 0.5 ml of formic acid. The reaction mixture is stirred at 80° C. for 16 hours and subsequently evaporated. The residue is partitioned between dichloromethane and saturated sodium hydrogencarbonate solution. The organic phase is dried over sodium sulfate and evaporated. The residue is chromatographed on a silica-gel column with dichloromethane/methanol as eluent: 5-[5-[1-(1-methyl-4-piperidyl)triazol-4-yl]-1H-pyrrolo-[2,3-b]pyridin-3-yl]-2-tetrahydropyran-4-yloxybenzonitrile as colourless solid; HPLC/MS (A): 1.75 min, [M+H] 484;

$^1$H NMR (500 MHz, DMSO-d$_6$) δ [ppm]=12.05 (d, J=2.1, 1H), 8.79 (d, J=1.9, 1H), 8.77 (s, 1H), 8.62 (d, J=1.7, 1H), 8.06 (d, J=2.3, 1H), 8.01 (dd, J=8.8, 2.3, 1H), 7.96 (d, J=2.6, 1H), 7.45 (d, J=8.9, 1H), 4.85 (tt, J=7.8, 3.8, 1H), 4.52 (m, 1H), 3.89 (m, 2H), 3.55 (ddd, J=11.4, 8.3, 3.1, 2H), 2.91 (d, J=9.3, 2H), 2.25 (s, 3H), 2.08 (m, 8H), 1.70 (dtd, J=12.3, 8.2, 3.8, 2H).

The following compounds are obtained analogously

| Compound No. | Structure and/or name | Analogous to synthesis example |
|---|---|---|
| "A24" | 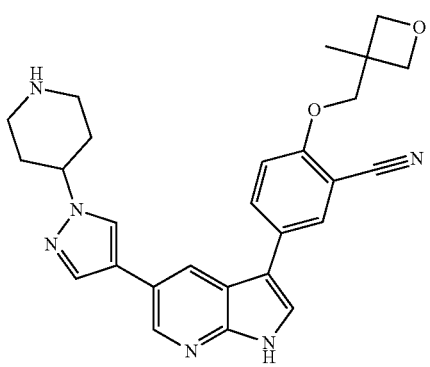 [SMILES: CC1(COc2ccc(-c3c[nH]c4ncc(-c5cnn(C6CCNCC6)c5)cc34)cc2C#N)COC1]<br><br>2-[(3-Methyloxetan-3-yl)methoxy]-5-[5-[1-(4-piperidyl)pyrazol-4-yl]-1H-pyrrolo[2,3-b]pyridin-3-yl]-benzonitrile<br><br>HPLC/MS (A): 1.81 min, [M + H] 469 | 6 |

-continued

| Compound No. | Structure and/or name | Analogous to synthesis example |
|---|---|---|
| "A25" | 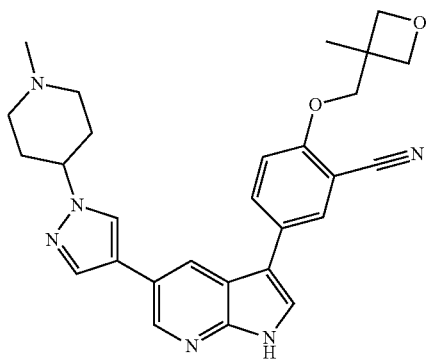 [SMILES: CN1CCC(n2cc(-c3cnc4[nH]cc(-c5ccc(OCC6(C)COC6)c(C#N)c5)c4c3)cn2)CC1]<br>2-[(3-Methyloxetan-3-yl)methoxy]-5-[5-[1-(1-methyl-4-piperidyl)pyrazol-4-yl]-1H-pyrrolo[2,3-b]pyridin-3-yl]-benzonitrile | 9 |
| "A26" | 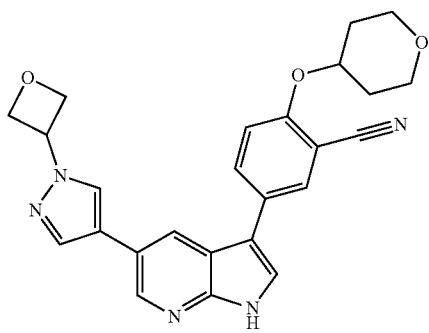 [SMILES: N#Cc1cc(-c2c[nH]c3ncc(-c4cnn(C5COC5)c4)cc23)ccc1OC1CCOCC1]<br>5-[5-[1-(Oxetan-3-yl)pyrazol-4-yl]-1H-pyrrolo[2,3-b]-pyridin-3-yl]-2-tetrahydropyran-4-yloxybenzonitrile<br>HPLC/MS (C): 1.65 min, [M + H] 442 | 4 |
| "A27" | 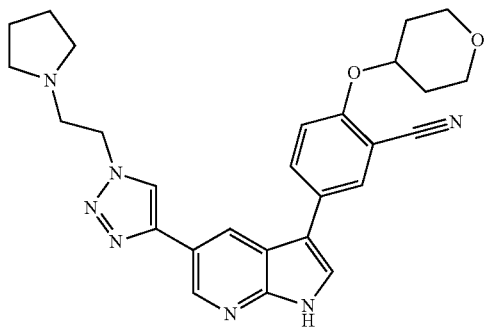 [SMILES: N#Cc1cc(-c2c[nH]c3ncc(-c4cn(CCN5CCCC5)nn4)cc23)ccc1OC1CCOCC1]<br>5-[5-[1-(2-Pyrrolidin-1-ylethyl)triazol-4-yl]-1H-pyrrolo-[2,3-b]pyridin-3-yl]-2-tetrahydropyran-4-yloxybenzo-nitrile<br>HPLC/MS (C): 1.37 min, [M + H] 484 | 13 |

-continued

| Compound No. | Structure and/or name | Analogous to synthesis example |
|---|---|---|
| "A28" | 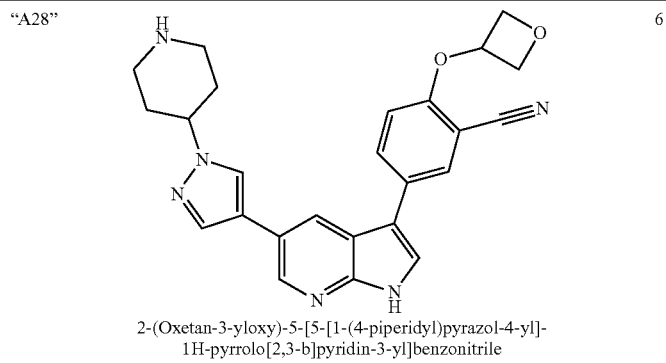
2-(Oxetan-3-yloxy)-5-[5-[1-(4-piperidyl)pyrazol-4-yl]-1H-pyrrolo[2,3-b]pyridin-3-yl]benzonitrile | 6 |
| "A29" | 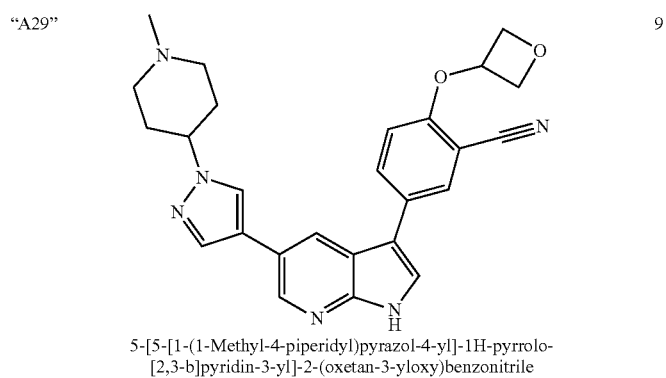
5-[5-[1-(1-Methyl-4-piperidyl)pyrazol-4-yl]-1H-pyrrolo-[2,3-b]pyridin-3-yl]-2-(oxetan-3-yloxy)benzonitrile | 9 |
| "A30" | 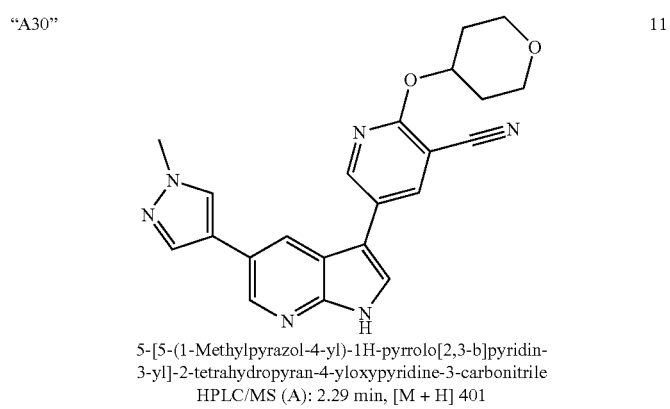
5-[5-(1-Methylpyrazol-4-yl)-1H-pyrrolo[2,3-b]pyridin-3-yl]-2-tetrahydropyran-4-yloxypyridine-3-carbonitrile
HPLC/MS (A): 2.29 min, [M + H] 401 | 11 |
| "A33" | 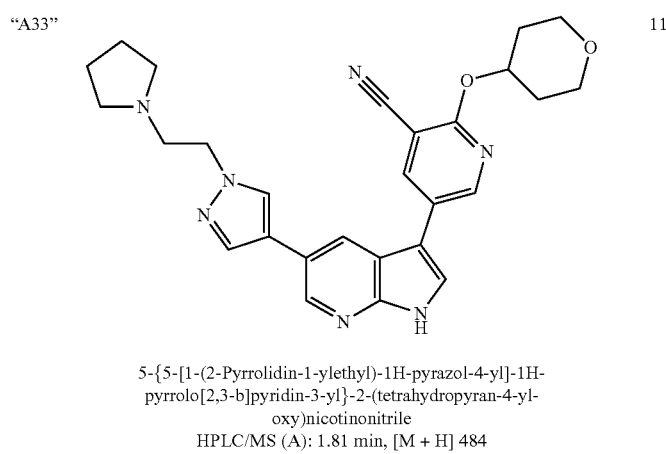
5-{5-[1-(2-Pyrrolidin-1-ylethyl)-1H-pyrazol-4-yl]-1H-pyrrolo[2,3-b]pyridin-3-yl}-2-(tetrahydropyran-4-yl-oxy)nicotinonitrile
HPLC/MS (A): 1.81 min, [M + H] 484 | 11 |

| Compound No. | Structure and/or name | Analogous to synthesis example |
|---|---|---|
| "A37" | 5-[5-(1-Oxetan-3-yl-1H-pyrazol-4-yl)-1H-pyrrolo-[2,3-b]pyridin-3-yl]-2-(tetrahydropyran-4-yloxy)-nicotinonitrile<br>HPLC/MS (A): 2.28 min, [M + H] 443 | 11 |
| "A38" | 5-{5-[1-(2-Methoxyethyl)-1H-pyrazol-4-yl]-1H-pyrrolo-[2,3-b]pyridin-3-yl}-2-(tetrahydropyran-4-yloxy)-nicotinonitrile<br>HPLC/MS (C): 1.70 min, [M + H] 445 | 11 |

EXAMPLE 14

The preparation of 5-[5-(1-methyl-1H-pyrazol-4-yl)-1H-pyrrolo[2,3-b]pyridin-3-yl]-2-(oxetan-3-yloxy)benzonitrile ("A31") is carried out analogously to the following scheme:

-continued

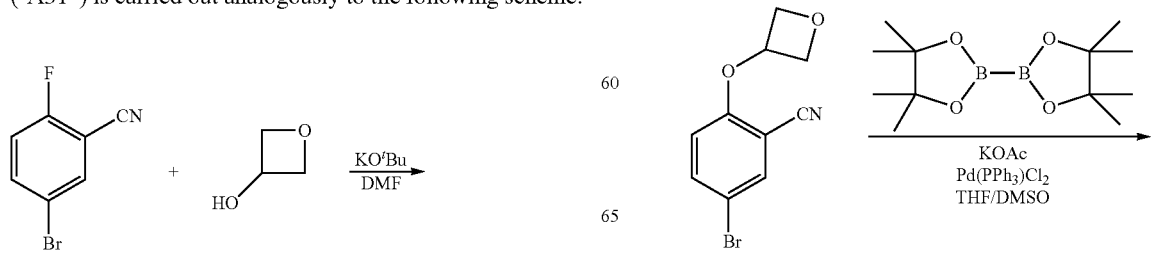

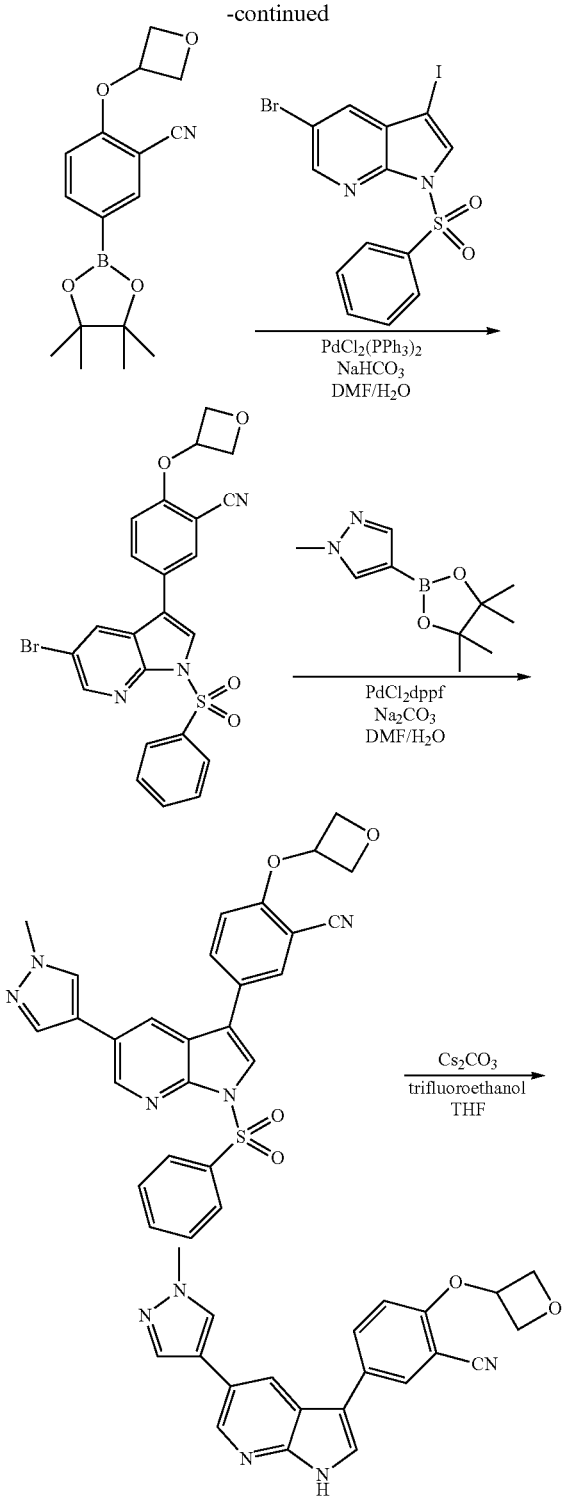

temperature for 16 hours. The reaction mixture is poured into 700 ml of water. The precipitate formed is filtered off with suction, washed with water and dried in vacuo: 5-bromo-2-(oxetan-3-yloxy)benzonitrile as white powder; HPLC/MS (A): 2.42 min, [M+H] 254/256.

7.46 g (76.0 mmol) of dry potassium acetate and 533 mg (0.76 mmol) of bis(triphenylphosphine)palladium(II) chloride are added to a solution, kept under nitrogen, of 9.66 g (38.0 mmol) of 5-bromo-2-(oxetan-3-yloxy)benzonitrile and 10.1 g (39.9 mmol) of bis(pinacoloto)diboron in 80 ml of THF, and the mixture is stirred at 80° C. for 16 hours. The reaction mixture is partitioned between water and dichloromethane. The organic phase is dried over sodium sulfate and evaporated. The residue is chromatographed on a silica-gel column with cyclohexane/ethyl acetate as eluent: 2-(oxetan-3-yloxy)-5-(4,4,5,5-tetramethyl-1,3,2-dioxaborolan-2-yl)benzonitrile as white crystals; HPLC/MS (A): 2.83 min, [M+H] 302;

$^1$H NMR (400 MHz, DMSO-$d_6$) δ [ppm] 7.91 (d, J=1.6, 1H), 7.86 (dd, J=8.5, 1.5, 1H), 6.90 (d, J=8.5, 1H), 5.48 (m, 1H), 4.97 (m, 2H), 4.58 (dd, J=7.8, 4.7, 2H), 1.29 (s, 12H).

A suspension, kept under nitrogen, of 4.63 g (10.0 mmol) of 1-(benzenesulfonyl)-5-bromo-3-iodopyrrolo[2,3-b]pyridine, 3.31 g (11.0 mmol) of 2-(oxetan-3-yloxy)-5-(4,4,5,5-tetramethyl-1,3,2-dioxaborolan-2-yl)benzonitrile and 1.01 g (12.0 mmol) of sodium hydrogencarbonate in 20 ml of DMF and 10 ml of water is warmed to 80° C. with stirring. 140 mg (0.20 mmol) of bis(triphenylphosphine)palladium(II) chloride are then added. The reaction mixture is stirred at 80° C. for 18 hours. The reaction mixture is cooled to room temperature, and water is added. The precipitate formed is filtered off with suction, washed with water and dried in vacuo. The crude product is crystallised from isopropanol: 5-(1-benzenesulfonyl-5-bromo-1H-pyrrolo[2,3-b]pyridin-3-yl)-2-(oxetan-3-yloxy)benzonitrile as pale-grey powder; HPLC/MS (A): 3.14 min, [M+H] 510/512.

A suspension, kept under nitrogen, of 510 mg (1.00 mmol) of 5-(1-benzenesulfonyl-5-bromo-1H-pyrrolo[2,3-b]pyridin-3-yl)-2-(oxetan-3-yloxy)benzonitrile, 229 g (1.10 mmol) of 1-methyl-4-(4,4,5,5-tetramethyl-1,3,2-dioxaborolan-2-yl)-1H-pyrazole and 127 mg (1.20 mmol) of sodium carbonate in 2 ml of DMF and 1 ml of water is warmed to 80° C. with stirring. 16 mg (0.02 mmol) of [1,1'-bis(diphenylphosphino)ferrocene]palladium(II) dichloride are then added. The reaction mixture is stirred at 80° C. for 20 hours. The reaction mixture is cooled to room temperature, and water is added. The precipitate formed is filtered off with suction, washed with water and chromatographed on a silicagel column with ethyl acetate/methanol as eluent: 5-[1-benzenesulfonyl-5-(1-methyl-1H-pyrazol-4-yl)-1H-pyrrolo[2,3-b]pyridin-3-yl]-2-(oxetan-3-yloxy)benzonitrile as pale-brown glass; HPLC/MS (C): 1.90 min, [M+H] 512.

2 ml of 2,2,2-trifluoroethanol and 642 mg (1.97 mmol) of caesium carbonate are added to a solution of 338 mg (0.66 mmol) of 5-[1-benzenesulfonyl-5-(1-methyl-1H-pyrazol-4-yl)-1H-pyrrolo[2,3-b]pyridin-3-yl]-2-(oxetan-3-yloxy)benzonitrile in 2 ml of THF, and the mixture is stirred at 80° C. for 16 hours. The reaction mixture is evaporated, and the residue is chromatographed on a silica-gel column with dichloromethane/methanol as eluent: 5-[5-(1-methyl-1H-pyrazol-4-yl)-1H-pyrrolo[2,3-b]pyridin-3-yl]-2-(oxetan-3-yloxy)benzonitrile as yellowish powder; HPLC/MS (C): 1.58 min, [M+H] 372;

$^1$H NMR (500 MHz, DMSO-$d_6$) δ [ppm] 11.92 (d, J=2.0, 1H), 8.52 (d, J=2.0, 1H), 8.35 (d, J=1.9, 1H), 8.22 (s, 1H), 8.12 (d, J=2.3, 1H), 8.02 (dd, J=8.7, 2.3, 1H), 7.97 (s, 1H), 6.73 g (60.0 mmol) of potassium tert-butoxide are added with external ice-cooling to a solution, kept under nitrogen, of 4.44 g (60.0 mmol) of 3-hydroxyoxetane in 50 ml of DMF. A solution of 10.0 g (50.0 mmol) of 5-bromo-2-fluorobenzonitrile in 50 ml of DMF is then added dropwise to the yellow solution formed, and the reaction mixture is stirred at room 7.91 (d, J=2.7, 1H), 6.94 (d, J=8.8, 1H), 5.50 (p, J=5.7, 1H), 5.00 (t, J=6.9, 2H), 4.64 (dd, J=7.7, 4.9, 2H), 3.89 (s, 3H).

An analogous procedure gives 2-(3-methyloxetan-3-yl-methoxy)-5-[5-(1-methyl-1H-pyrazol-4-yl)-1H-pyrrolo[2,3-b]pyridin-3-yl]benzonitrile ("A32"), beige powder; HPLC/MS (A): 2.26 min, [M+H] 400;

¹H NMR (500 MHz, DMSO-d₆) δ [ppm] 11.91 (s, 1H), 8.53 (d, J=2.0, 1H), 8.36 (d, J=2.0, 1H), 8.23 (s, 1H), 8.07 (dq, J=4.6, 2.3, 2H), 7.98 (s, 1H), 7.91 (d, J=1.2, 1H), 7.38 (d, J=9.5, 1H), 4.55 (d, J=5.8, 2H), 4.35 (d, J=5.9, 2H), 4.29 (s, 2H), 3.89 (s, 3H), 1.43 (s, 3H).

EXAMPLE 15

The preparation of 2-(oxetan-3-yloxy)-5-[5-(1-oxetan-3-yl-1H-pyrazol-4-yl)-1H-pyrrolo-[2,3-b]pyridin-3-yl]benzonitrile ("A34") is carried out analogously to the following scheme:

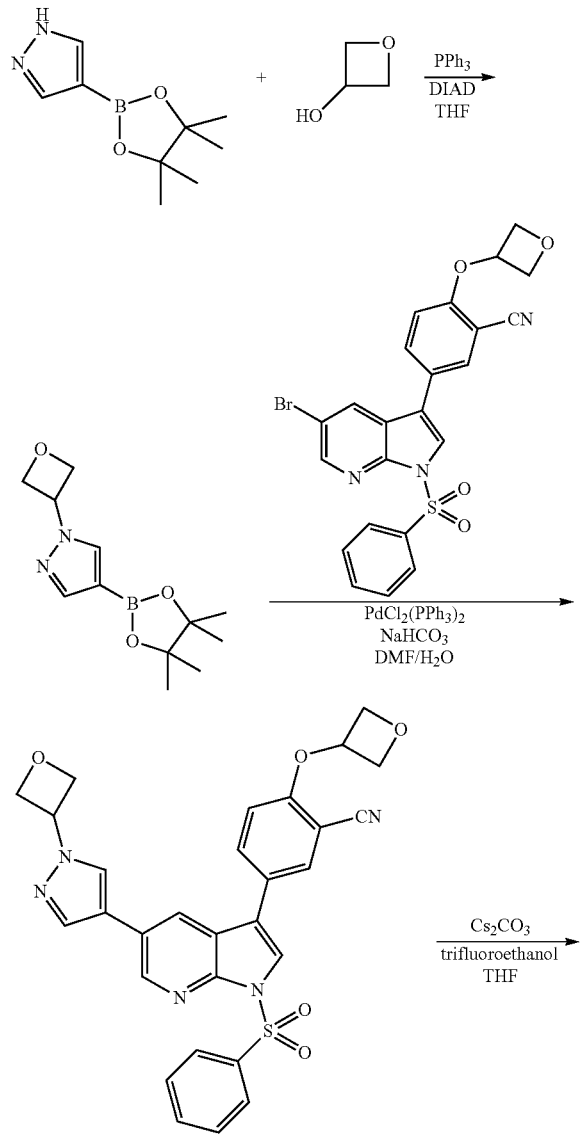

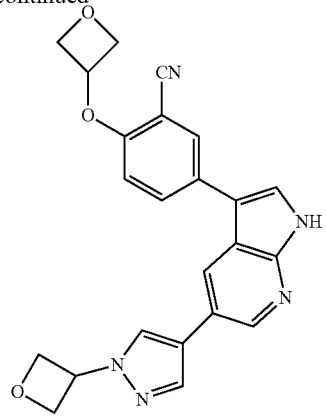

4.76 ml (24.0 mmol) of diisopropyl azodicarboxylate are added dropwise to a solution of 3.88 g (20.0 mmol) of pinacolyl pyrazole-4-boronate, 1.78 g (48.0 mmol) of oxetan-3-ol and 6.29 g (24.0 mmol) of triphenylphosphine in 40 ml of THF. The reaction mixture is stirred at room temperature for 16 hours. A further 1.78 g (48.0 mmol) of oxetan-3-ol, 6.29 g (24.0 mmol) of triphenylphosphine and 3.00 ml (15.1 mmol) of diisopropyl azodicarboxylate are then added, and the reaction mixture is stirred at room temperature for 3 days. The reaction mixture is evaporated, and the residue is taken up in cyclohexane. The precipitate formed is filtered off with suction and washed with cyclohexane. The filtrate is evaporated, and the residue is chromatographed on a silica-gel column with cyclohexane/ethyl acetate as eluent: 1-oxetan-3-yl-4-(4,4,5,5-tetramethyl-1,3,2-dioxaborolan-2-yl)-1H-pyrazole as yellow oil; HPLC/MS (A): 2.10 min, [M+H] 251; ¹H NMR (400 MHz, DMSO-d₆) δ [ppm] 8.07 (s, 1H), 7.72 (s, 1H), 5.60 (p, J=6.9, 1H), 4.89 (m, 4H), 1.25 (s, 12H).

A suspension, kept under nitrogen, of 357 mg (0.70 mmol) of 5-(1-benzenesulfonyl-5-bromo-1H-pyrrolo[2,3-b]pyridin-3-yl)-2-(oxetan-3-yloxy)benzonitrile, 385 mg (1.54 mmol) of 1-oxetan-3-yl-4-(4,4,5,5-tetramethyl-1,3,2-dioxaborolan-2-yl)-1H-pyrazole and 141 mg (1.68 mmol) of sodium hydrogencarbonate in 2 ml of DMF and 1 ml of water is warmed to 80° C. with stirring. 20 mg (0.028 mmol) of bis(triphenyl-phosphine)palladium(II) chloride are then added. The reaction mixture is stirred at 80° C. for 44 hours. The reaction mixture is cooled to room temperature, and water is added. The precipitate formed is filtered off with suction, washed with water and chromatographed on a silica-gel column with ethyl acetate/methanol as eluent: 5-[1-benzenesulfonyl-5-(1-oxetan-3-yl-1H-pyrazol-4-yl)-1H-pyrrolo[2,3-b]pyridin-3-yl]-2-(oxetan-3-yloxy)benzonitrile as yellowish foam; HPLC/MS (C): 1.89 min, [M+H] 554.

2 ml of 2,2,2-trifluoroethanol and 441 mg (1.97 mmol) of caesium carbonate are added to a solution of 249 mg (0.45 mmol) of 5-[1-benzenesulfonyl-5-(1-oxetan-3-yl-1H-pyrazol-4-yl)-1H-pyrrolo[2,3-b]pyridin-3-yl]-2-(oxetan-3-yloxy)benzonitrile in 3 ml of THF, and the mixture is stirred at 80° C. for 16 hours. The reaction mixture is evaporated, taken up in water and filtered. The residue is washed with water, dried and recrystallised from dimethyl sulfoxide: 2-(oxetan-3-yloxy)-5-[5-(1-oxetan-3-yl-1H-pyrazol-4-yl)-1H-pyrrolo[2,3-b]pyridin-3-yl]benzonitrile as white crystals; HPLC/MS (C): 1.59 min, [M+H] 414;

¹H NMR (500 MHz, DMSO-d₆) δ [ppm] 11.95 (s, 1H), 8.57 (d, J=1.7, 1H), 8.49 (s, 1H), 8.41 (d, J=1.6, 1H), 8.15 (s, 1H), 8.13 (d, J=2.1, 1H), 8.03 (dd, J=8.7, 2.2, 1H), 7.92 (d, J=2.3, 1H), 6.95 (d, J=8.8, 1H), 5.61 (p, J=7.0, 1H), 5.50 (m, 1H), 5.00 (m, 2H), 4.96 (m, 4H), 4.64 (dd, J=7.3, 5.0, 2H).

EXAMPLE 16

The preparation of 2-(3-methyloxetan-3-ylmethoxy)-5-[5-(1-oxetan-3-yl-1H-pyrazol-4-yl)-1H-pyrrolo[2,3-1D]pyridin-3-yl]benzonitrile ("A35") and 2-(3-methyloxetan-3-ylmethoxy)-5-[5-(1H-pyrazol-4-yl)-1H-pyrrolo[2,3-b]pyridin-3-yl]benzonitrile ("A36") is carried out analogously to the following scheme:

A suspension, kept under nitrogen, of 377 mg (0.70 mmol) of 5-(1-benzenesulfonyl-5-bromo-1H-pyrrolo[2,3-b]pyridin-3-yl)-2-(3-methyloxetan-3-ylmethoxy)benzonitrile, 367 mg (1.47 mmol) of 1-oxetan-3-yl-4-(4,4,5,5-tetramethyl-1,3,2-dioxaborolan-2-yl)-1H-pyrazole and 118 mg (1.40 mmol) of sodium hydrogencarbonate in 1.4 ml of DMF and 0.7 ml of water is warmed to 40° C. with stirring. 20 mg (0.03 mmol) of bis(triphenylphosphine)palladium(II) chloride are then added. The reaction mixture is heated to 80° C. and stirred at this temperature for 44 hours. The reaction mixture is cooled to room temperature, and water is added. The precipitate

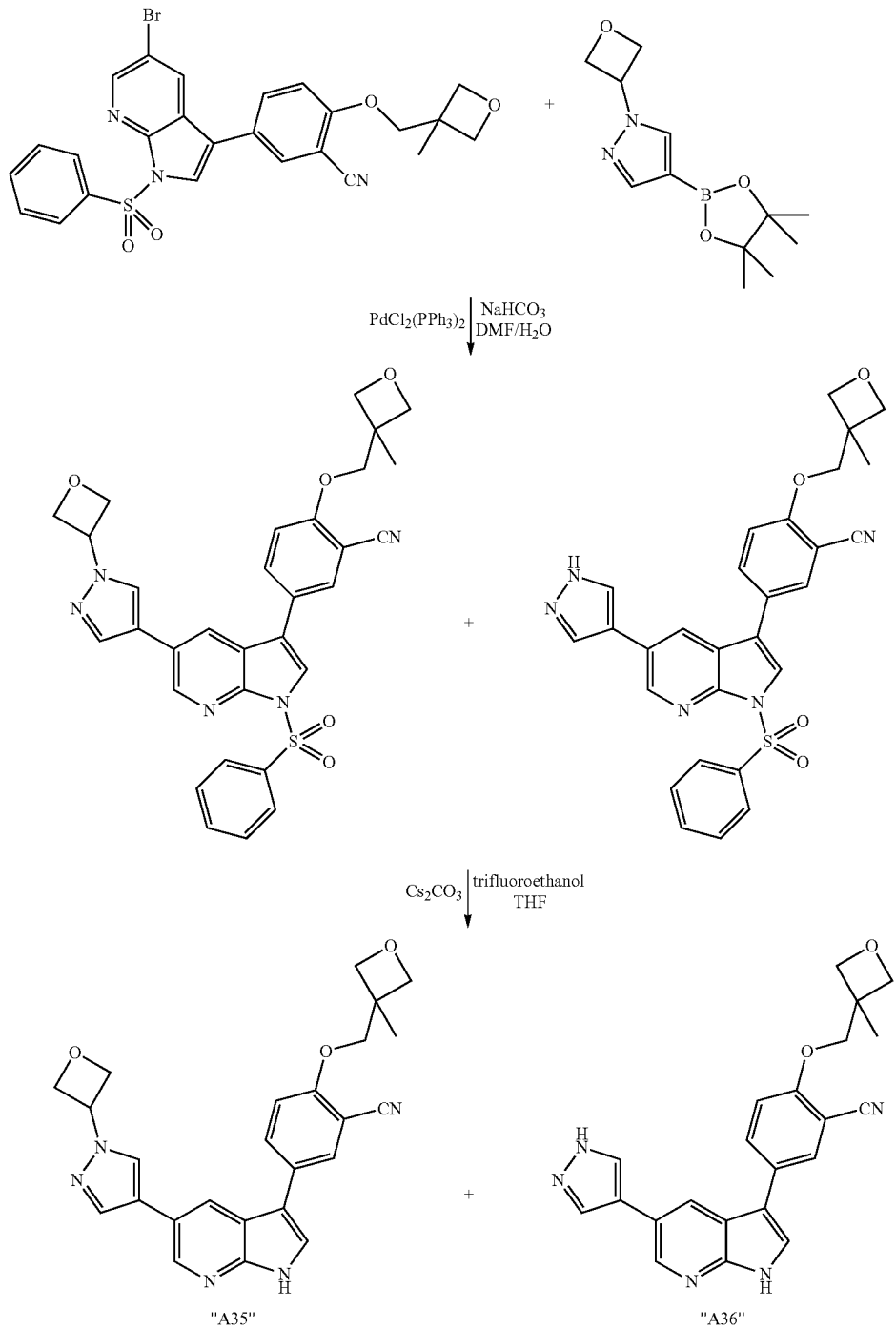

formed is filtered off with suction, washed with water and chromatographed on a silica-gel column with ethyl acetate/methanol as eluent: mixture of 5-[1-benzenesulfonyl-5-(1-oxetan-3-yl-1H-pyrazol-4-yl)-1H-pyrrolo[2,3-b]pyridin-3-yl]-2-(3-methyloxetan-3-ylmethoxy)benzonitrile {HPLC/MS (B): 2.82 min, [M+H] 582} and 5-[1-benzenesulfonyl-5-(1H-pyrazol-4-yl)-1H-pyrrolo[2,3-b]pyridin-3-yl]-2-(3-methyloxetan-3-ylmethoxy)benzonitrile {HPLC/MS (B): 2.71 min, [M+H] 526} as white foam; amount 371 mg.

The mixture obtained in this way is suspended in 2.6 ml of THF and 2.6 ml of 2,2,2-trifluoroethanol, and 530 mg (1.63 mmol) of caesium carbonate are added. The suspension is stirred at 80° C. for 3 hours. The reaction mixture is evaporated, and the residue is chromatographed on a silica-gel column with dichloromethane/methanol as eluent, giving two products:

2-(3-methyloxetan-3-ylmethoxy)-5-[5-(1-oxetan-3-yl-1H-pyrazol-4-yl)-1H-pyrrolo[2,3-b]-pyridin-3-yl]benzonitrile as white powder; HPLC/MS (B): 2.26 min, [M+H] 442;

$^1$H NMR (400 MHz, DMSO-$d_6$) δ [ppm] 11.94 (s, 1H), 8.57 (d, J=2.0, 1H), 8.49 (s, 1H), 8.41 (d, J=2.0, 1H), 8.15 (s, 1H), 8.09 (m, 3H), 7.92 (d, J=1.3, 1H), 7.38 (d, J=9.5, 1H), 5.61 (p, J=6.9, 1H), 4.96 (m, 4H), 4.55 (d, J=5.8, 2H), 4.35 (d, J=5.9, 2H), 4.29 (s, 2H), 1.43 (s, 3H);

2-(3-methyloxetan-3-ylmethoxy)-5-[5-(1H-pyrazol-4-yl)-1H-pyrrolo[2,3-b]pyridin-3-yl]-benzonitrile as beige powder; HPLC/MS (B): 2.14 min, [M+H] 386;

$^1$H NMR (400 MHz, DMSO-$d_6$) δ [ppm] 11.90 (d, J=2.1, 1H), 8.57 (d, J=1.9, 1H), 8.40 (d, J=1.8, 1H), 8.17 (bs, 2H), 8.08 (m, 2H), 7.91 (d, J=2.6, 1H), 7.38 (d, J=9.5, 1H), 4.55 (d, J=5.8, 2H), 4.35 (d, J=5.9, 2H), 4.29 (s, 2H), 1.43 (s, 3H).

$IC_{50}$ values of TBK1- and IKKε-inhibiting compounds according to the invention

| Compound No. | TBK1 enzyme assay $IC_{50}$ [nM] | IKKε enzyme assay $IC_{50}$ [nM] | TBK1 + IKKε cell assay $IC_{50}$ [nM] |
|---|---|---|---|
| "A1" | A | A | C |
| "A2" | B | B | |
| "A3" | C | C | |
| "A4" | A | A | B |
| "A5" | C | C | |
| "A6" | A | B | |
| "A7" | A | A | B |
| "A8" | A | A | C |
| "A9" | A | A | B |
| "A10" | A | A | A |
| "A11" | A | B | |
| "A12" | A | A | B |
| "A13" | A | A | C |
| "A14" | C | C | |
| "A15" | A | A | A |
| "A16" | A | A | A |
| "A17" | B | B | C |
| "A18" | A | A | B |
| "A19" | B | B | |
| "A20" | A | A | B |
| "A21" | A | A | B |
| "A22" | A | A | B |
| "A23" | A | A | B |
| "A24" | A | A | B |
| "A26" | A | A | A |
| "A27" | A | A | B |
| "A30" | A | A | B |
| "A31" | A | A | C |
| "A32" | A | A | B |
| "A33" | A | A | B |
| "A34" | A | A | C |
| "A35" | A | A | B |
| "A36" | A | A | C |
| "A37" | A | A | C |
| "A38" | A | A | B |

$IC_{50}$:
<0.3 μM = A
0.3-3 μM = B
3-50 μM = C

The following examples relate to medicaments:

EXAMPLE A

Injection Vials

A solution of 100 g of an active compound according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound according to the invention with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound according to the invention, 9.38 g of $NaH_2PO_4$.2 $H_2O$, 28.48 g of $Na_2HPO_4$.12 $H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound according to the invention are mixed with 99.5 g of Vaseline under aseptic conditions.

EXAMPLE E

Tablets

A mixture of 1 kg of active compound, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active compound are introduced into hard gelatine capsules in a conventional manner in such a way that each capsule contains 20 mg of the active compound.

EXAMPLE H

Ampoules

A solution of 1 kg of an active compound according to the invention in 60 l of bidistilled water is sterile-filtered, transferred into ampoules, lyophilised under sterile conditions and sealed under sterile conditions. Each ampoule contains 10 mg of active compound.

The invention claimed is:

1. A compound of formula I

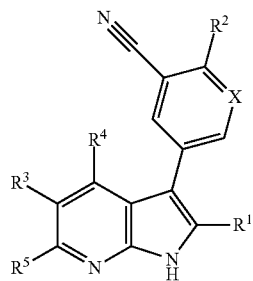

I in which
X denotes CH or N,
$R^1$ denotes H, A or Cyc,
$R^2$ denotes $O[C(R^6)_2]_n Het^1$ or $O[C(R^6)_2]_n Cyc$,
$R^3$ denotes $O[C(R6)_2]_n Het^2$, Ar or $Het^2$,
$R^4$ denotes H or $OR^6$,
$R^5$ denotes H or $OR^6$,
$R^6$ denotes H or methyl,
$Het^1$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydro-pyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n A$, $S(O)_n Ar$, or A,
$Het^2$ denotes dihydropyrrolyl, pyrrolidinyl, azetidinyl, tetrahydroimidazolyl, tetra-hydrofuranyl, dihydropyrazolyl, tetrahydropyrazolyl, dihydropyridyl, tetrahydropyridyl, dihydropyranyl, tetrahydropyranyl, piperidinyl, morpholinyl, hexa-hydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by A, $[C(R^6)_2]_p OR^6$, or $[C(R^6)_2]_p Het^1$,
Ar denotes phenyl or naphthyl, each of which is unsubstituted or monosubstituted by $[C(R^6)_2]_p Het^1$ or CN,
A denotes unbranched or branched alkyl having 1-8 C atoms, in which one or two non-adjacent CH and/or $CH_2$ groups may each be replaced by N or O atoms and/or, in addition, 1-7 H atoms may each be replaced by F or Cl,
Cyc denotes cyclic alkyl having 3, 4, 5, 6 or 7 C atoms which is unsubstituted or monosubstituted by CN or A,
Hal denotes F, Cl, Br or I, m denotes 1, 2 or 3,
n denotes 0, 1 or 2, and
p denotes 0, 1, 2, 3 or 4, or a pharmaceutically usable salt, tautomer or stereoisomer thereof, including mixtures thereof in all ratios.

2. The compound according to claim 1, wherein $R^2$ denotes $O[C(R^6)_2]_n Het^1$.

3. The compound according to claim 1, wherein $R^3$ denotes $O[C(R^6)_2]_n Het^2$.

4. The compound according to claim 1, wherein $Het^1$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by A.

5. The compound according to claim 1, wherein $Het^2$ denotes dihydropyrrolyl, pyrrolidinyl, azetidinyl, tetrahydroimidazolyl, tetrahydrofuranyl, dihydropyrazolyl, tetrahydropyrazolyl, dihydropyridyl, tetrahydropyridyl, dihydropyranyl, tetrahydropyranyl, piperidinyl, morpholinyl, hexahydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzo-dioxolyl, benzothiophenyl, benzofuranyl, imidazopyridyl or furo[3,2-b]pyridyl, each of which is unsubstituted or monosubstituted by A.

6. The compound according to claim 1, wherein Ar denotes phenyl or naphthyl, each of which is unsubstituted or monosubstituted by CN.

7. The compound according to claim 1, wherein A denotes unbranched or branched alkyl having 1-8 C atoms, in which 1-7 H atoms may each be replaced by F.

8. A compound according to claim 1, selected from

| Compound No. | Name |
| --- | --- |
| "A4" | 5-[5-(1-Methylpyrazol-4-yl)-1H-pyrrolo[2,3-b]pyridin-3-yl]-2-tetrahydropyran-4-yloxybenzonitrile |
| "A6" | 5-[5-(4-Cyanophenyl)-1H-pyrrolo[2,3-b]pyridin-3-yl]-2-tetrahydropyran-4-yloxybenzonitrile |
| "A7" | 5-[5-[1-(2-Morpholinoethyl)pyrazol-4-yl]-1H-pyrrolo[2,3-b]pyridin-3-yl]-2-tetrahydropyran-4-yloxybenzonitrile |
| "A8" | 5-[5-(4-Morpholinophenyl)-1H-pyrrolo[2,3-b]pyridin-3-yl]-2-tetrahydropyran-4-yloxybenzonitrile |
| "A9" | 5-[5-[1-(2-Pyrrolidin-1-ylethyl)pyrazol-4-yl]-1H-pyrrolo[2,3-b]pyridin-3-yl]-2-tetrahydropyran-4-yloxybenzonitrile |
| "A10" | 5-[5-[1-(2-Methoxyethyl)pyrazol-4-yl]-1H-pyrrolo[2,3-b]pyridin-3-yl]-2-tetrahydropyran-4-yloxybenzonitrile |
| "A11" | 5-[2-Methyl-5-(1-methylpyrazol-4-yl)-1H-pyrrolo[2,3-b]pyridin-3-yl]-2-tetrahydropyran-4-yloxybenzonitrile |
| "A12" | 5-[5-(1-Piperidin-4-yl-1H-pyrazol-4-yl)-1H-pyrrolo[2,3-b]pyridin-3-yl]-2-(tetrahydropyran-4-yloxy)benzonitrile |
| "A13" | 2-(1-Methylpiperidin-4-yloxy)-5-[5-(1-methyl-1H-pyrazol-4-yl)-1H-pyrrolo[2,3-b]pyridin-3-yl]benzonitrile |
| "A14" | 5-(5-Bromo-1H-pyrrolo[2,3-b]pyridin-3-yl)-2-(cyclopropylmethoxy)benzonitrile |
| "A15" | 5-[5-[1-(2-Hydroxyethyl)pyrazol-4-yl]-1H-pyrrolo[2,3-b]pyridin-3-yl]-2-tetrahydropyran-4-yloxybenzonitrile |
| "A16" | 5-[5-[1-(1-Methyl-4-piperidyl)pyrazol-4-yl]-1H-pyrrolo[2,3-b]pyridin-3-yl]-2-tetrahydropyran-4-yloxybenzonitrile |
| "A17" | 5-[5-(4-Methylpiperazin-1-yl)-1H-pyrrolo[2,3-b]pyridin-3-yl]-2-tetrahydropyran-4-yloxybenzonitrile |
| "A18" | 5-[5-[1-(4-Piperidyl)pyrazol-4-yl]-1H-pyrrolo[2,3-b]pyridin-3-yl]-2-tetrahydropyran-4-yloxypyridine-3-carbonitrile |
| "A19" | 5-[5-[1-[1-(Benzenesulfonyl)-4-piperidyl]pyrazol-4-yl]-1H-pyrrolo[2,3-b]pyridin-3-yl]-2-tetrahydropyran-4-yloxypyridine-3-carbonitrile |
| "A20" | 5-[5-[1-(1-Methyl-4-piperidyl)pyrazol-4-yl]-1H-pyrrolo[2,3-b]pyridin-3-yl]-2-tetrahydropyran-4-yloxybenzonitrile |
| "A21" | 5-[5-(2-Morpholinoethoxy)-1H-pyrrolo[2,3-b]pyridin-3-yl]-2-tetrahydropyran-4-yloxybenzonitrile |
| "A22" | 5-[5-[1-(4-Piperidyl)triazol-4-yl]-1H-pyrrolo[2,3-b]pyridin-3-yl]-2-tetrahydropyran-4-yloxybenzonitrile |
| "A23" | 5-[5-[1-(1-Methyl-4-piperidyl)triazol-4-yl]-1H-pyrrolo[2,3-b]pyridin-3-yl]-2-tetrahydropyran-4-yloxybenzonitrile |
| "A24" | 2-[(3-Methyloxetan-3-yl)methoxy]-5-[5-[1-(4-piperidyl)pyrazol-4-yl]-1H-pyrrolo[2,3-b]pyridin-3-yl]benzonitrile |
| "A25" | 2-[(3-Methyloxetan-3-yl)methoxy]-5-[5-[1-(1-methyl-4-piperidyl)pyrazol-4-yl]-1H-pyrrolo[2,3-b]pyridin-3-yl]benzonitrile |
| "A26" | 5-[5-[1-(Oxetan-3-yl)pyrazol-4-yl]-1H-pyrrolo[2,3-b]pyridin-3-yl]-2-tetrahydropyran-4-yloxybenzonitrile |
| "A27" | 5-[5-[1-(2-Pyrrolidin-1-ylethyl)triazol-4-yl]-1H-pyrrolo[2,3-b]pyridin-3-yl]-2-tetrahydropyran-4-yloxybenzonitrile |
| "A28" | 2-(Oxetan-3-yloxy)-5-[5-[1-(4-piperidyl)pyrazol-4-yl]-1H-pyrrolo[2,3-b]pyridin-3-yl]benzonitrile |
| "A29" | 5-[5-[1-(1-Methyl-4-piperidyl)pyrazol-4-yl]-1H-pyrrolo[2,3-b]pyridin-3-yl]-2-(oxetan-3-yloxy)benzonitrile |
| "A30" | 5-[5-(1-Methylpyrazol-4-yl)-1H-pyrrolo[2,3-b]pyridin-3-yl]-2-tetrahydropyran-4-yloxypyridine-3-carbonitrile |
| "A31" | 5-[5-(1-Methyl-1H-pyrazol-4-yl)-1H-pyrrolo[2,3-b]pyridin-3-yl]-2-(oxetan-3-yloxy)benzonitrile |

| Compound No. | Name |
|---|---|
| "A32" | 2-(3-Methyloxetan-3-ylmethoxy)-5-[5-(1-methyl-1H-pyrazol-4-yl)-1H-pyrrolo[2,3-b]pyridin-3-yl]benzonitrile |
| "A33" | 5-{5-[1-(2-Pyrrolidin-1-ylethyl)-1H-pyrazol-4-yl]-1H-pyrrolo-[2,3-b]pyridin-3-yl}-2-(tetrahydropyran-4-yloxy)nicotinonitrile |
| "A34" | 2-(Oxetan-3-yloxy)-5-[5-(1-oxetan-3-yl-1H-pyrazol-4-yl)-1H-pyrrolo[2,3-b]pyridin-3-yl]benzonitrile |
| "A35" | 2-(3-Methyloxetan-3-ylmethoxy)-5-[5-(1-oxetan-3-yl-1H-pyrazol-4-yl)-1H-pyrrolo[2,3-b]pyridin-3-yl]benzonitrile |
| "A36" | 2-(3-Methyloxetan-3-ylmethoxy)-5-[5-(1H-pyrazol-4-yl)-1H-pyrrolo[2,3-b]pyridin-3-yl]benzonitrile |
| "A37" | 5-[5-(1-Oxetan-3-yl-1H-pyrazol-4-yl)-1H-pyrrolo[2,3-b]pyridin-3-yl]-2-(tetrahydropyran-4-yloxy)nicotinonitrile |
| "A38" | 5-{5-[1-(2-Methoxyethyl)-1H-pyrazol-4-yl]-1H-pyrrolo[2,3-b]pyridin-3-yl}-2-(tetrahydropyran-4-yloxy)nicotinonitrile | and pharmaceutically usable salts, tautomers and stereoisomers thereof, including mixtures thereof in all ratios.

9. A medicament composition comprising at least one compound of the formula I according to claim 1 and/or a pharmaceutically usable salt, tautomer or stereo-isomer thereof, including mixtures thereof in all ratios, and at least one excipient and/or adjuvant.

10. A compound of formula II

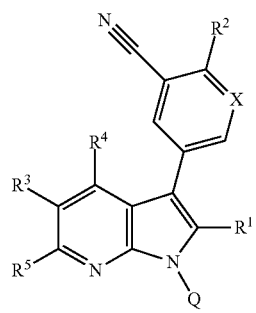

in which
X denotes CH or N,
Q denotes tert-butoxycarbonyl or phenylsulfonyl,
$R^1$ denotes H, A or Cyc,
$R^2$ denotes $O[C(R^6)_2]_n Het^1$ or $O[C(R^6)_2]_n Cyc$,
$R^3$ denotes H, Hal, $O[C(R^6)_2]_n Het^2$, Ar or $Het^2$,
$R^4$ denotes H or $OR^6$,
$R^5$ denotes H or $OR^6$,
$R^6$ denotes H or methyl,
$Het^1$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydro-pyridyl, piperidinyl, morpholinyl, hexahydropyridazinyl, hexahydropyrimidinyl, 1,3-dioxolanyl, tetrahydropyranyl or piperazinyl, each of which is unsubstituted or monosubstituted by $S(O)_n A$, $S(O)_n Ar$ or A,
$Het^2$ denotes dihydropyrrolyl, pyrrolidinyl, azetidinyl, tetrahydroimidazolyl, tetra-hydrofuranyl, dihydropyrazolyl, tetrahydropyrazolyl, dihydropyridyl, tetrahydro-pyridyl, dihydropyranyl, tetrahydropyranyl, piperidinyl, morpholinyl, hexa-hydropyridazinyl, hexahydropyrimidinyl, 1,3-dioxolanyl, piperazinyl, furyl, thienyl, pyrrolyl, imidazolyl, pyrazolyl, oxazolyl, isoxazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or monosubstituted by A, $[C(R^6)_2]_p OR^6$ or $[C(R^6)_2]_p Het^1$,
Ar denotes phenyl or naphthyl, each of which is unsubstituted or monosubstituted by $[C(R^6)_2]_p Het^1$ or CN,
A denotes unbranched or branched alkyl having 1-8 C atoms, in which one or two non-adjacent CH and/or $CH_2$ groups may each be replaced by N or O atoms and/or, in addition, 1-7 H atoms may each be replaced by F,
Cyc denotes cyclic alkyl having 3, 4, 5, 6 or 7 C atoms which is unsubstituted or monosubstituted by CN or A,
Hal denotes F, Cl, Br or I,
m denotes 1, 2 or 3,
n denotes 0, 1 or 2, and
p denotes 0, 1, 2, 3 or 4,
or a pharmaceutically usable salt, tautomer or stereoisomer thereof, including mixtures thereof in all ratios.

11. The compound according to claim 1, wherein
$R^1$ denotes H or A,
$R^2$ denotes $O[C(R^6)_2]_n Het^1$ or $O[C(R^6)_2]_n Cyc$,
$R^3$ denotes $O[C(R^6)_2]_n Het^2$, Ar or $Het^2$,
$R^4$ denotes H,
$R^5$ denotes H, and
$R^6$ denotes H or methyl.

12. The compound according to claim 1, wherein $Het^1$ denotes pyrrolidinyl, oxetanyl, piperidinyl, morpholinyl, tetrahydropyranyl or piperazinyl, each of which is unsubstituted or monosubstituted by $S(O)_n A$, $S(O)_n Ar$ or A.

13. The compound according to claim 1, wherein $Het^2$ denotes piperidinyl, morpholinyl, piperazinyl, pyrazolyl, or triazolyl, each of which is unsubstituted or monosubstituted by A, $[C(R^6)_2]_p OR^6$ or $[C(R^6)_2]_p Het^1$.

14. A process for the preparation of compounds of the formula I according to claim 1 and pharmaceutically usable salts, tautomers and stereoisomers thereof, said process comprising:
reacting a compound of formula IV

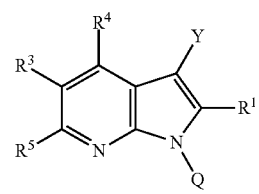

in which $R^1$, $R^3$, $R^4$, $R^5$ have the meanings indicated in claim 1,

Y denotes Br or I, and
Q denotes a protecting group,
with a compound of formula III
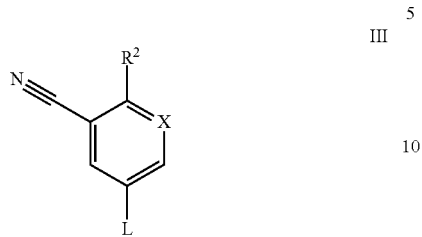
III
in which X and $R^2$ have the meanings indicated in claim 1, and
L denotes a boronic acid radical or a boronic acid ester group,
and subsequently cleaving off Q;
and/or converting a base or acid compound of formula I into one of its pharmaceutically usable salts.
\* \* \* \* \*

```
                        SEQUENCE LISTING

<160> NUMBER OF SEQ ID NOS: 2

<210> SEQ ID NO 1
<211> LENGTH: 23
<212> TYPE: PRT
<213> ORGANISM: Artificial Sequence
<220> FEATURE:
<223> OTHER INFORMATION: Biotin-Ah-Ah-

<400> SEQUENCE: 1

Ala Lys Pro Lys Gly Asn Lys Asp Tyr His Leu Gln Thr Cys Cys Gly
1               5                   10                  15

Ser Leu Ala Tyr Arg Arg Arg
            20

<210> SEQ ID NO 2
<211> LENGTH: 23
<212> TYPE: PRT
<213> ORGANISM: Artificial Sequence
<220> FEATURE:
<223> OTHER INFORMATION: Biotin-C6-C6-

<400> SEQUENCE: 2

Gly Leu Lys Lys Glu Arg Leu Leu Asp Asp Arg His Asp Ser Gly Leu
1               5                   10                  15

Asp Ser Met Lys Asp Glu Glu
            20
```